United States Patent
Liu et al.

(10) Patent No.: US 11,337,832 B2
(45) Date of Patent: May 24, 2022

(54) SOCKET-SUSPENSION MONITORING SYSTEM FOR AMPUTEES

(71) Applicant: NORTH CAROLINA STATE UNIVERSITY, Raleigh, NC (US)

(72) Inventors: Ming Liu, Cary, NC (US); He Huang, Cary, NC (US)

(73) Assignee: North Carolina State University, Raleigh, NC (US)

(*) Notice: Subject to any disclaimer, the term of this patent is extended or adjusted under 35 U.S.C. 154(b) by 35 days.

(21) Appl. No.: 16/496,756

(22) PCT Filed: Mar. 23, 2018

(86) PCT No.: PCT/US2018/024163
§ 371 (c)(1),
(2) Date: Sep. 23, 2019

(87) PCT Pub. No.: WO2018/175977
PCT Pub. Date: Sep. 27, 2018

(65) Prior Publication Data
US 2020/0022825 A1    Jan. 23, 2020

Related U.S. Application Data

(60) Provisional application No. 62/475,517, filed on Mar. 23, 2017.

(51) Int. Cl.
*A61F 2/76* (2006.01)
*A61F 2/60* (2006.01)
(Continued)

(52) U.S. Cl.
CPC .................. *A61F 2/76* (2013.01); *A61F 2/60* (2013.01); *A61F 2/80* (2013.01); *G01D 5/16* (2013.01); *A61F 2002/763* (2013.01)

(58) Field of Classification Search
CPC ...... A61F 2/76; A61F 2/80; A61F 2/60; A61F 2/6607; A61F 2002/763; A61F 2002/762;
(Continued)

(56) References Cited

U.S. PATENT DOCUMENTS 7,850,740 B2  12/2010  Cox et al.
7,922,773 B1  4/2011   Kuiken
(Continued)

FOREIGN PATENT DOCUMENTS

GB   2302949 A      2/1997
WO   2016036846 A1  3/2016

OTHER PUBLICATIONS

PCT International Search Report and Written Opinion in International Application No. PCT/US2018/024163, dated Jun. 28, 2018, 6 pages.

(Continued)

*Primary Examiner* — Christie L Bahena
(74) *Attorney, Agent, or Firm* — Meunier Carlin & Curfman LLC

(57) ABSTRACT

A continuous socket/suspension monitoring system according to principles of the present invention tracks relative displacement between amputee residuum and their socket using magnetic sensors. The system includes at least one magnetic sensor in a liner worn on the amputees' residuum which correspond to sensors provide in or on the prosthesis socket. The system allows for monitoring of pistoning continuously during locomotion and does not require socket modification, is safe to amputee patients, is easy to use, and is low cost.

9 Claims, 17 Drawing Sheets

(51) Int. Cl.
*A61F 2/80* (2006.01)
*G01D 5/16* (2006.01)

(58) Field of Classification Search
CPC ...... A61F 2002/6863; A61F 2002/6607; A61F 2002/488; G01D 5/16
See application file for complete search history.

(56) References Cited

U.S. PATENT DOCUMENTS

| | | |
|---|---|---|
| 8,206,459 B1 | 6/2012 | Lock et al. |
| 2008/0114270 A1* | 5/2008 | DiSilvestro .......... A61B 5/4528 600/595 |

OTHER PUBLICATIONS

Extended European Search Report issued in EP 18771187.4, dated Jan. 19, 2021, 7 pages.

\* cited by examiner

SOCKET-SUSPENSION MONITORING SYSTEM FOR AMPUTEES

ACKNOWLEDGEMENTS

This invention was made with government support under Grants 90BI0034 awarded by the National Institute on Disability, Independent Living, and Rehabilitation Research (NIDILRR). The government has certain rights in the invention.

BACKGROUND OF THE INVENTION

Field of the Invention

Embodiments of the present invention relate to socket suspension monitoring system for prosthetics, specifically a substantially continuous monitoring system.

Background

Amputation is a still common procedure and usually relates to high lifetime medical cost. In U.S. 185,000 amputations are performed annually. The highest number of amputee patients are over sixty-five years old. In 2010, about 73,000 non-traumatic lower-limb amputations were performed in adults aged 20 years or older with diagnosed diabetes. A Department of Veterans Affairs study showed the average lifetime cost for prosthetics and medical care for loss of a single leg for a veteran of the Iraq or Afghanistan wars was more than $1.4 million.

Lower limb amputees account for about 84% of the 1.7 million amputees in the US now and must rely on prosthetic legs to regain upright locomotion. Prosthetic sockets and related suspension systems serve as the sole interface between the amputees' residuum and prosthesis and play key roles in amputees' health and functionality. A well fitted socket will help amputees achieve satisfactory load transmission, stability, and efficient control for mobility. Additionally, an efficient suspension system prevents large relative motion between the socket and the residuum.

Lower limb amputees rely on prosthetic sockets and suspension systems to interface with their prostheses. Complications due to ill-fitting sockets include abnormal gait patterns, high energy consumption during locomotion, and repeated skin damage, as shown in FIG. 1. Various prostheses are shown in FIG. 2 and lower leg anatomy is shown in FIG. 3 for reference. In addition, the volume of the stump changes throughout the day. An example stump is shown in FIG. 4. Ill-fitting sockets may lead to negative health impacts and on the independence of amputees.

Although prosthetic socket-suspension systems are carefully designed by well-trained professionals, there is no guarantee that socket fit and suspension system efficiency will be maintained for a long period of time. The rigid socket cannot adapt to residuum volume changes, which include 1) long term changes related with body weight and 2) short term changes, such shrinkage caused by repeated loading on residuum or swelling after locomotion due to weakened vascular systems related with diabetes. Consequently, sockets can turn to ill-fitted and the suspension system can lose its efficiency.

Ill-fitting sockets and inefficient suspension systems have negative impacts on the health and independence of amputees. An ill-fitting socket can cause intolerable high pressure on the residuum, and an inefficient suspension system can cause a lot of rubbing/friction between the socket and the residuum leading to skin abrasions. Both intolerable high pressure and friction on the residuum 1) force amputees to adopt inefficient gait patterns, which decrease their mobility and contribute to secondary injuries (e.g. osteoarthritis on the intact side, osteopenia on the prosthetic side, back pain, 2) cause skin damage, which is hard to heal and prevents amputees from using their prosthetic legs. This decrease in mobility and injuries limit the independence of the lower limb amputees and binds them to wheelchairs.

Currently, the socket fit and suspension efficiency are monitored by the amputees alone. This self-monitoring approach has its limitations: 1) amputees with neuropathy are not capable of this approach. But, neuropathy is very common among elderly amputees and patients with diabetes, which is the number one reason of amputation in US. Amputees that suffer from neuropathy are instructed to inspect their residuum routinely, both visually and tactually, for skin damage. Due to high physical and psychological burden related with frequent donning/doffing of their socket, amputees with neuropathy usually do not manage their residuum well and suffer repeated skin damage. Some amputees even have to give up their prostheses totally. 2) Results from the self-monitoring approach are very subjective, and monitoring accuracy is hard to evaluate or improve. Skin issues continue to be one of the highest concerns for amputees.

Continuous monitoring of socket suspension is also critical for clinicians and prosthetists to conduct preventive interventions. Currently, any information related with socket fit and suspension efficiency in amputees' daily life outside of the clinic is solely based on the user's feedback, which is subjective, possibly inaccurate/inconsistent, and usually deferred. Objective, quantitative information is critical and more useful for clinicians and prosthetists to understand interaction between the socket and residuum during amputees' daily life. The information collected from a continuous monitoring system can also be used to identify amputees' lifestyle changes. For example, a dramatic drop of prosthesis usage frequency may indicate other health and social issues. With this information, clinicians and prosthetists will be able to make prompt clinical decisions and intervene in an earlier stage to prevent injury, diagnose health issues, and provide consultations.

Measuring the pistoning is challenging because of the opacity and rigidity of prosthetic sockets. Several studies used radiography methods to assess the positions of bony structures within the residual limb relative to the socket wall. However, ionizing radiation-based studies were mostly restricted to static pistoning analysis and exposed subject to unnecessary radiation. The equipment used in these studies is also very expensive and is not readily available to clinicians and prosthetists. Recently, pistoning at the stump-socket interface is being measured by tracking the position of markers, attached to the liner, using photographic and optical motion capture methods. Optical motion capture methods require a transparent socket to access the markers inside the socket. Therefore, this method cannot be used to evaluated patients' often opaque everyday sockets. Non-contact photoelectric sensors were also recently used to evaluate dynamic pistoning. To accommodate the sensors, some major modifications, such as drilling holes on the socket, were needed. Such modifications are often costly and lead to permanent socket damage.

BRIEF SUMMARY OF THE INVENTION

Accordingly, the present invention is directed to a socket-suspension monitoring system and method for amputees that obviates one or more of the problems due to limitations and disadvantages of the related art.

An advantage of the present invention is to provide a monitoring system for amputees that have a prosthesis having a socket, where the system includes a residuum cover or liner, at least one magnet affixed to the residuum cover or liner and a plurality of magnetic sensors in the socket.

In another aspect of the present invention, a method of monitoring motion of a residuum in a prosthesis, where the residuum is covered by a liner or cover including at least one magnet and the prosthesis includes a plurality of magnetic sensors, includes identifying a location of the magnet in proximity to at least one of the magnetic sensors; and identifying displacement of the magnet from the at least one magnetic sensor.

Further embodiments, features, and advantages of the socket-suspension monitoring system, as well as the structure and operation of the various embodiments of the socket-suspension monitoring system, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate socket-suspension monitoring system. Together with the description, the figures further serve to explain the principles of the socket-suspension monitoring system described herein and thereby enable a person skilled in the pertinent art to make and use the socket-suspension monitoring system.

DETAILED DESCRIPTION OF THE INVENTION

Figure 1:
FIG. 1 is a photo showing example damage to a residuum from an ill-fitting sock or prosthesis.
Figure 2:
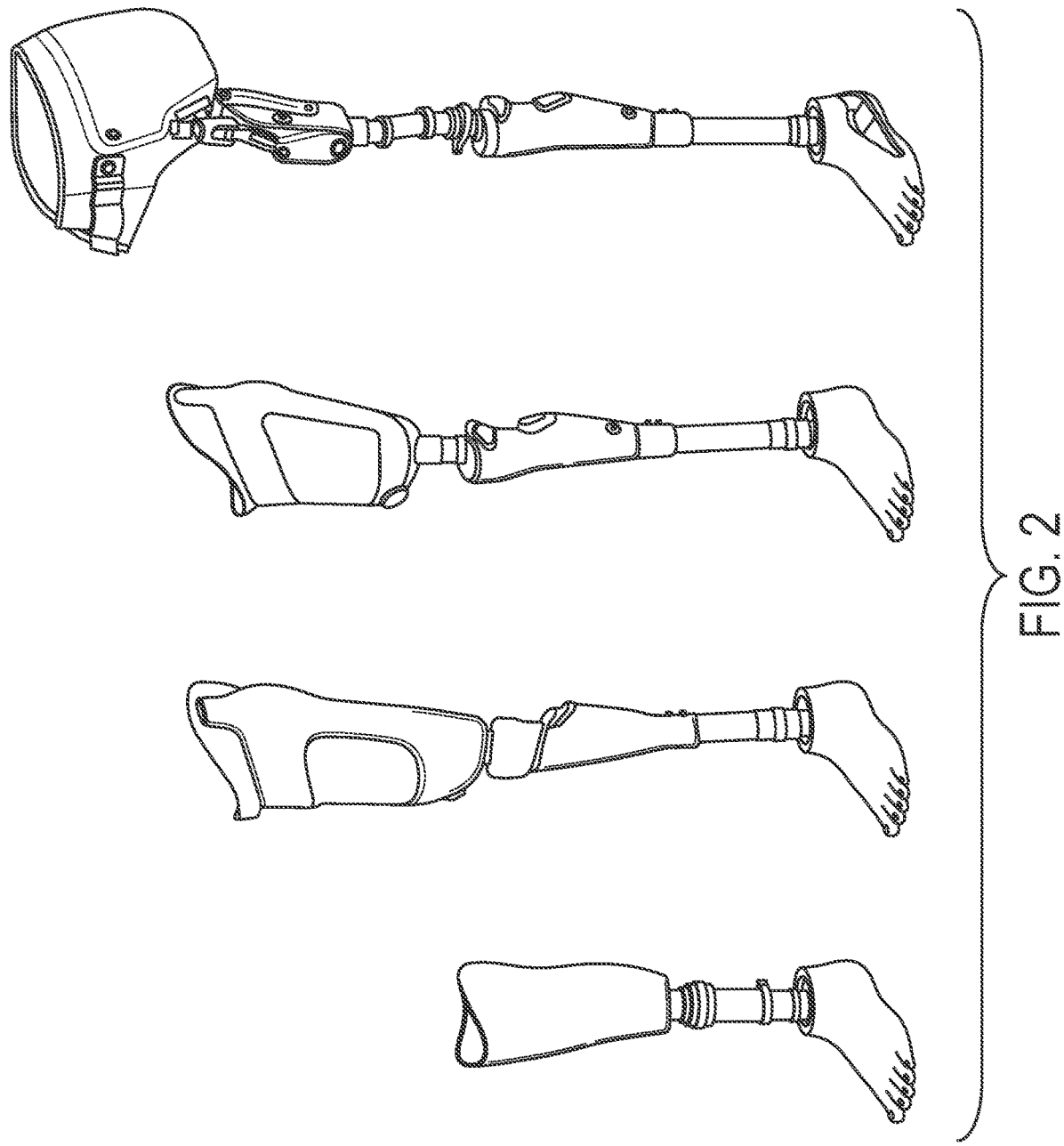
FIG. 2 shows various prostheses.
Figure 3:
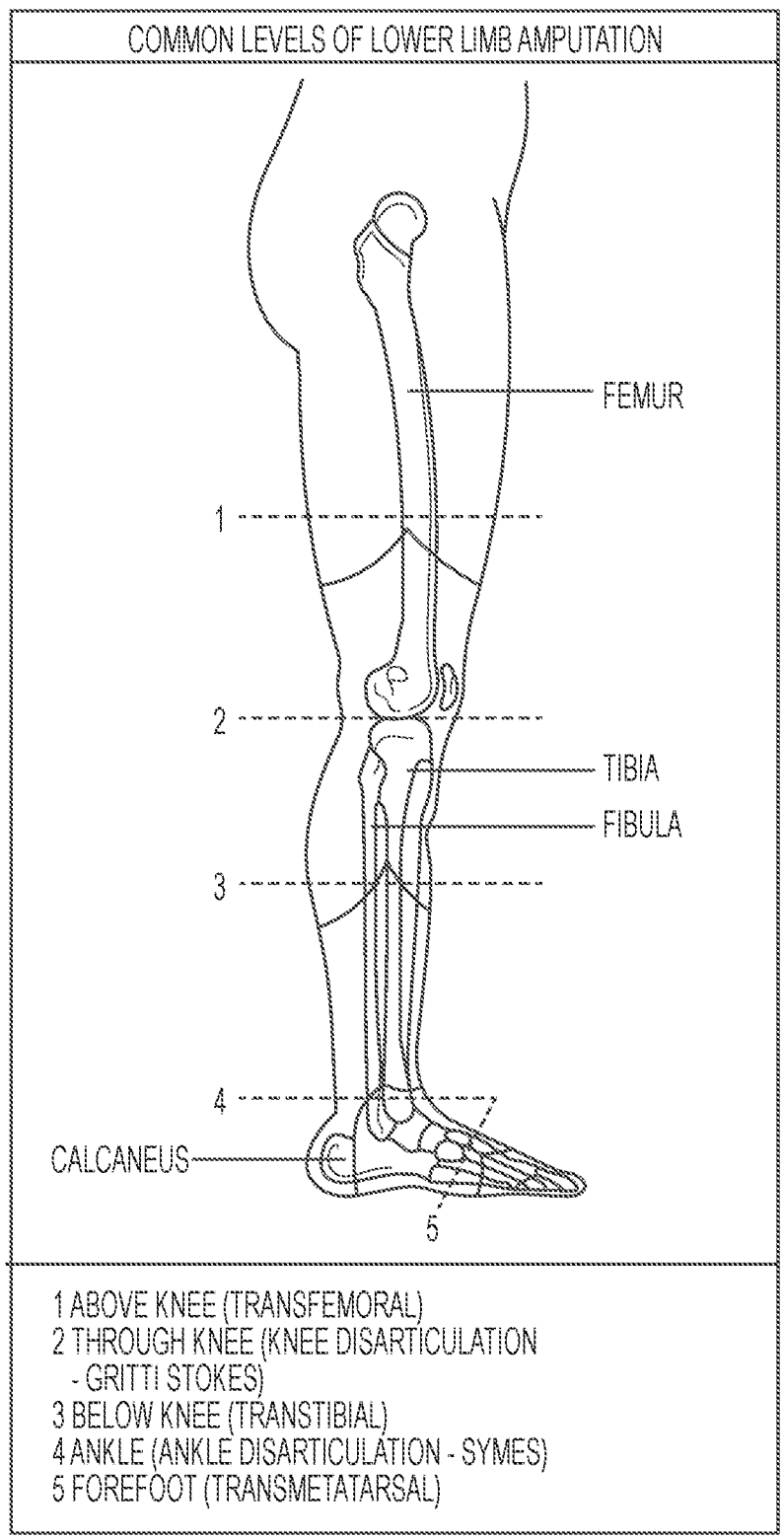
FIG. 3 shows lower leg anatomy.
Figure 4:
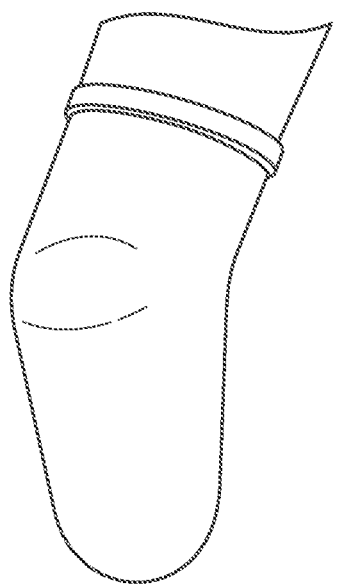
FIG. 4 shows an example stump.

Reference will now be made in detail to embodiments of the socket-suspension monitoring system with reference to the accompanying figures.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Continuously monitoring the socket fit and suspension can provide key information for amputees, clinicians and prosthetists to avoid health issues through early intervention. According to principles of the present invention, substantially continuous monitoring can be achieved at a lower cost than currently available monitoring.

In an aspect of the present invention, magnetic sensors on the sock sits tightly to the residual limb. The magnetic sensors in the sock are intended to cooperate with or correspond to a sensor in the prosthetic, which allows for monitoring and measurement of displacement of the limb with respect to the prosthetic and can provide information, such as how the interface "rubs" or otherwise is performing.

For example, a socket/suspension monitoring system according to principles of the present invention tracks relative displacement between amputee residuum and their socket using magnetic sensors. With information provided by the sensor system, clinicians and prosthetists will be able to make prompt clinical decisions and intervene in an earlier stage to prevent injury, diagnose health issues, and provide consultations.

Continuously monitoring socket fit and suspension efficiency provides key information for amputees, clinicians, and prosthetists to avoid health issues through early intervention. However, no products currently on the market can be used for continuous monitoring in everyday life.

According to principles of the present invention, a low-cost, wearable, easy to use, continuous socket/suspension is provided by tracking relative displacement between an amputee's residuum and their socket (pistoning) using magnetic sensors.

Continuous monitoring is the important to minimize the negative impact caused by the ill-fitting sockets and inefficient suspension systems, so prompt interventions from amputees and/or prosthetists and clinicians is possible. For small residuum changes, amputees can add/subtract prosthetic sock; for larger and more long-term residuum changes, prosthetists and clinicians can change the padding or reconstruct the socket.

According to principles of the present invention, a magnetic field is generated by at least one tiny permanent magnet attached on the liner (as the active marker). A magnetic sensor array attached on, for example, the external surface of the socket measures displacement of the marker. Compared with existing systems, this active marker tracking system is useful because: 1) it does not affect the integrity of the socket because sockets does not block the magnetic field generated by the marker, 2) it can be attached to any existing roll-on liner directly without modification of the existing socket suspension system; and 3) it can be achieved using generic, low-cost sensors. All of these features make this pistoning measuring system wearable, affordable, and easy to mount and use.

Figure 5:
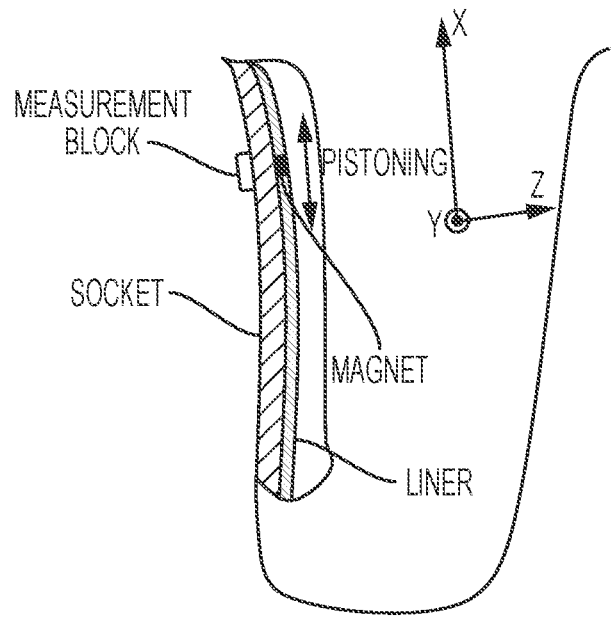
FIG. 5 illustrates an embodiment of a monitoring systems according to principles of the present invention.

FIG. 5 illustrates an embodiment of a monitoring systems according to principles of the present invention. A small magnet is attached on the external surface of the liner, i.e., the side of the liner opposite the side that abuts the patient's skin. The magnet moves with the residual limb inside the prosthetic socket. The relative displacement between the liner and the socket is measured by monitoring the location of the magnet using a measurement block, which is attached outside of the prosthetic socket.

The magnet in this example is a small Neodymium magnet disk with diameter 5 mm and thickness 2 mm (shown in FIG. 6), but may be any magnet suitably sized and available for use with the corresponding sensor system. An electromagnet may be used and might enable a better sensor system. However, the use of an electromagnet requires a power supply for the electromagnet, which must be adapted to be included in a tight and dynamic environment.

Figure 6:
FIG. 6 shows an exemplary magnet for use in an embodiment of the present invention.
Figure 6:
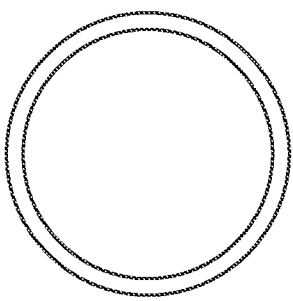

As illustrated in FIG. 6, the magnet may be sized smaller than a U.S. quarter dollar coin, or smaller. In the embodiment illustrated in FIG. 5, which uses a permanent magnet, the magnet does not need external excitation or power supply to generate the magnetic field needed to track its locations. The magnet is stuck on the external surface of the liner by a suitable adhesive, such as Tuf-Skin®, which is used to avoid potential damage to the liner during the mounting/unmounting procedure. Other attachment methods could be used to affix the magnet in or to the liner, such as bonding, encasing, sewing, etc. The magnet could also be included in the liner when the liner is fabricated or cast or embedded in a prosthetic sock, which is attached to the liner. As could be appreciated, the magnets could be included in the prosthesis, while the sensors could be provided on the liner.

The measurement block of the illustrated embodiment includes a sensor array and multiple amplifiers and is tethered to a standard data acquisition (DAQ) board. The system may be untethered, e.g. with a wireless module that can transfer the collected data to a mobile platform, such as a cell phone, tablet or other mobile processor. In the illustrated embodiment, the sensor array is made of multiple anisotropic magnetoresistive (AMR) sensors, AAT001-10E, from NVE (Eden Prairie, Minn.) to measure the magnetic field generated by the magnet. Similar sensors are widely found in smart phones. Other appropriate sensors may be used.

Figure 7:
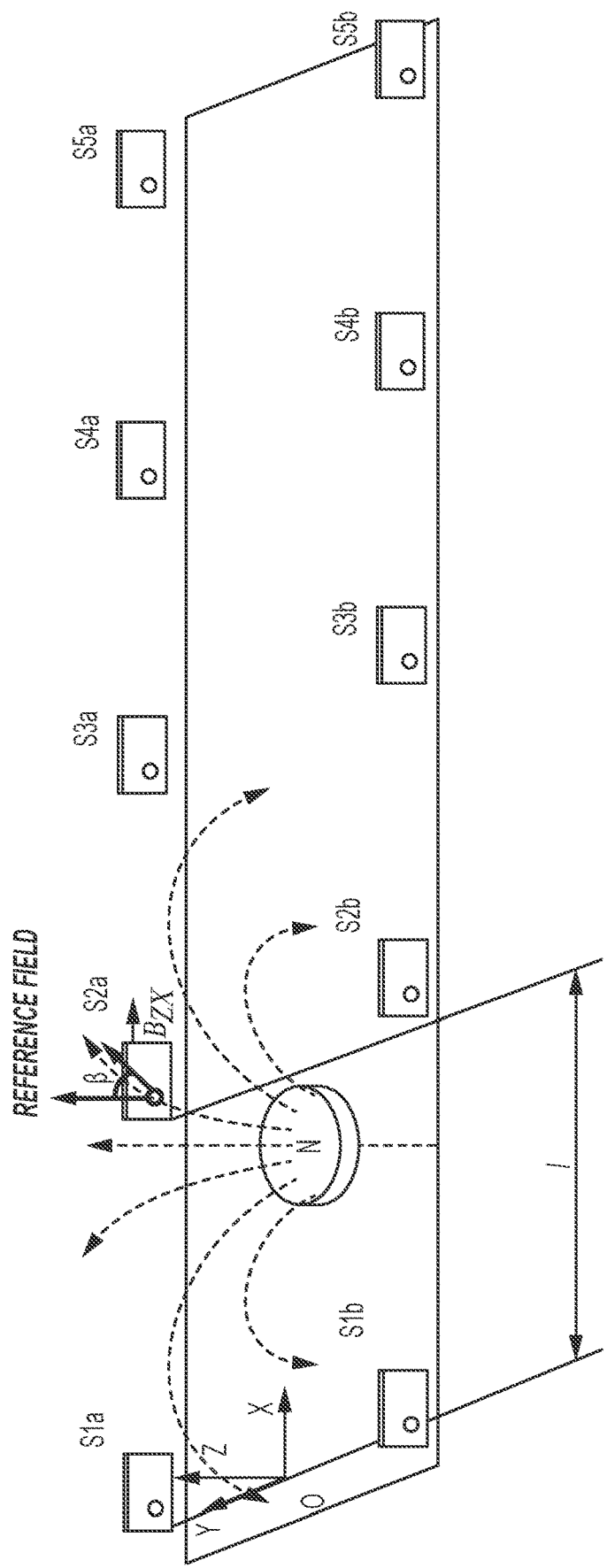
FIG. 7 shows an exemplary arrangement of sensor elements in an exemplary embodiment of the present invention.

Based on the recommendation from NVE, INA118, a Low Power Instrumentation Amplifier for Texas Instrument or its compatible, is used to amplify the signals collected from the magnetic sensors. The INA118 can be driven with 5V DC power supply and very low power is needed for operating the amplifiers (less than 0.002 W for each amplifier). Signals collected from the measurement block will be transferred to a DAQ board, which may be mounted on a personal computer, for example. The measurement box/block is glued or bandaged on external surface of the prosthetic socket. An exemplary magnet and sensor block is illustrated in FIG. 7. In FIG. 7, an exemplary arrangement of sensor elements is shown in with "circles" indicating the top surface of the magnetic angle sensor elements.

Due to the limitation on the measurement range of each sensor element, the sensor elements are arranged to maximize the measurement range of the socket-suspension monitoring system to minimize everyday calibration efforts. In testing, to ensure that normal pistoning could be measured by the sensor element array, the measurement range was set as 25.4 mm along distal-proximal direction (double the acceptable pistoning range). Five sensor elements are aligned in a row to cover this measurement range (see FIG. 7). In FIG. 7, white dots indicate the top surface of the magnetic angle sensor elements.

Embodiments of the present invention are not limited to the sensor designs described above, which is but an example of the sensor designs. The key information collected by the sensor system is the relative distance between the sensor element and magnet. The distance measurement can be used by measuring the amplitude of magnetic density, orientation of magnetic density, or combination of both. The array setup is to reach a balance between the accuracy and comfort to the patient. Magnetic sensor elements have a tracking range for a given magnet. The range usually increases with the size of the magnet. Measurement accuracy may be limited to improve patient comfort in that a smaller magnet may not always be in the range of the sensor. However, large magnets will not be conformable for the patient to wear. To track a small magnet, a sensor array may be used to ensure the magnet is trackable for at least one or two sensors.

At the same time, the distance of the sensor elements is known. This array setup could improve measurement accuracy by fusing data collected from different sensors. However, there is also a balance between accuracy and cost of the sensor system.

Similarly, the electronic processing chips or printed circuit board described herein are merely exemplary, and other such devices could be substituted according to principles of the present invention.

Figure 8A:
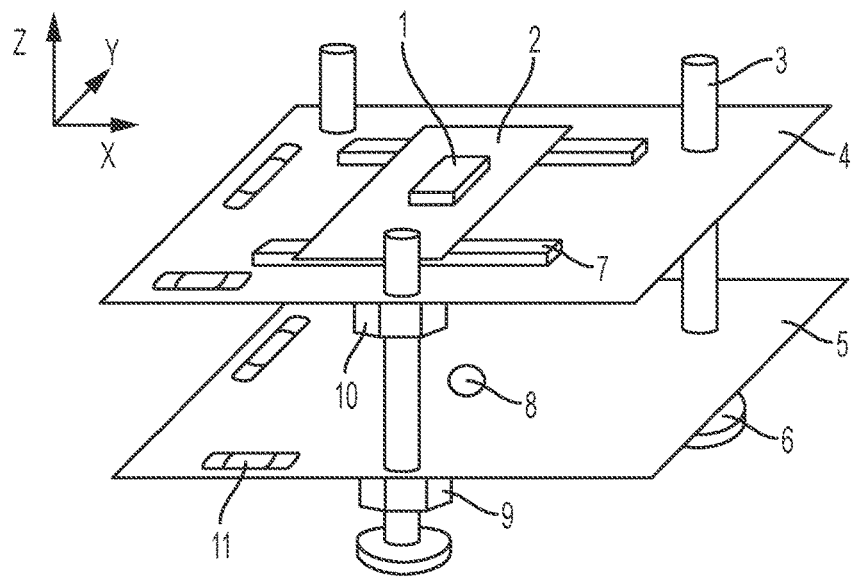
FIG. 8A shows an exemplary design of a sensor calibration platform according to principles of the present invention.
Figure 8B:
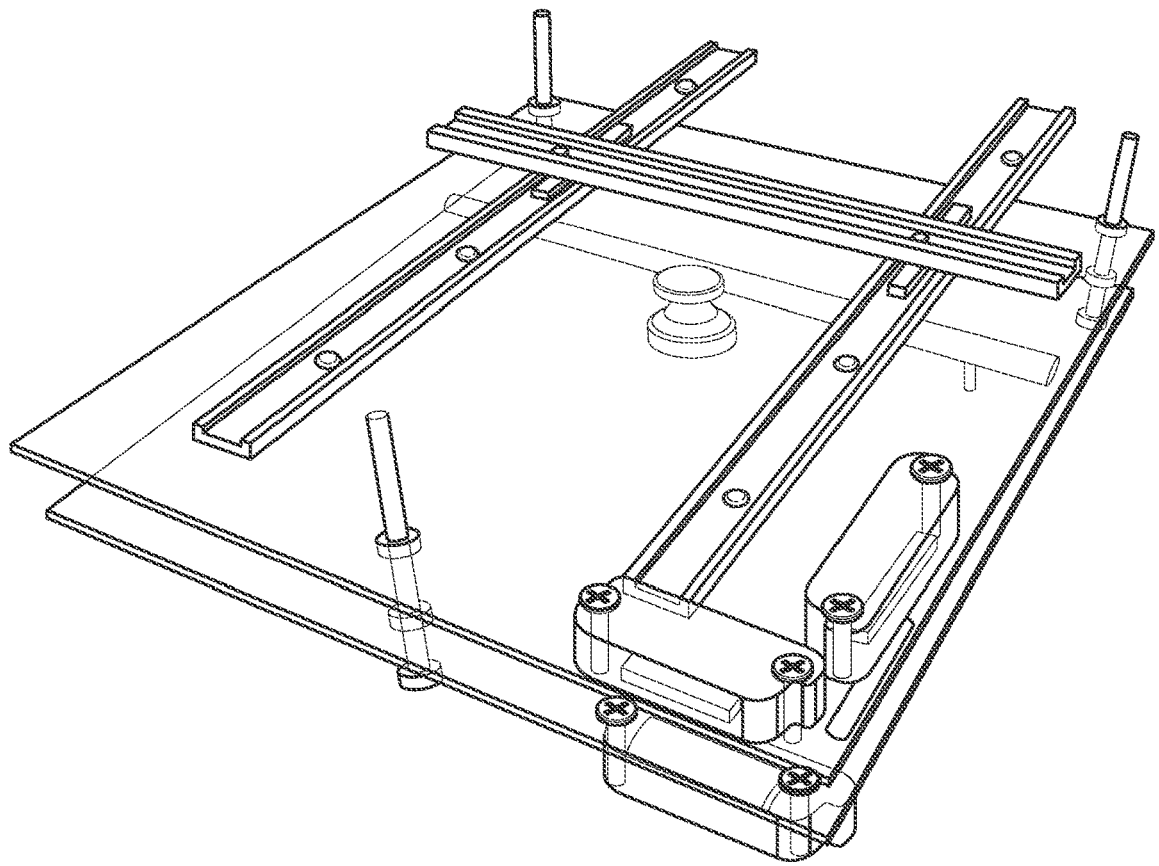
FIG. 8B shows a prototype of the calibration platform.

Sensors according to the principles of the present invention may be calibrated on a testing platform. An exemplary design of a sensor calibration platform is shown in FIG. 8A. As illustrated, the exemplary calibration platform includes 1: sensor block; 2, slider; 3, screw; 4, top base; 5, bottom base; 6, feet; 7, rail; 8, magnet; 9, bottom nut; 10, top nut; and 11, bubble level. (This drawing is used to demonstrate the basic concept and does not reflect the accurate dimensions.) The testing platform allows continuous sensor-magnet distance adjustments along the x- and z-axis. Discrete adjustments along the y-direction can be made by changing the mounting position on the slider. A constructed testing platform is shown in FIG. 8B.

The testing platform includes two bases. The magnet is fixed on the bottom base and the sensor block is fixed on a slider, which slides along two rails mounted on the top base. Three screws are used to support the two bases on three feet. By rotating the nuts on the screws and using bubble levels, the two bases can be leveled and the distance between the bottom base and the top base adjusted. All the components, except the rails, nuts, and screws, are made of plastic, and all the metal parts are arranged far away from the sensor and the magnet to avoid additional magnetic noise.

A good alignment between the magnet sensor block and the magnet improves accuracy of the measurement of socket pistoning. The sensor alignment procedure was conducted using a phantomic magnetic marker.

The mounting procedure may be conducted as follows:
1) Glue the magnet on the liner using Tuf-Skin® at the specified location.
2) Ask the amputee to support his/her full body weight with the prosthesis so that the residuum is in its deepest location in the socket.
3) Move a small magnetic disc on the external surface of the socket until the disc is stuck to the magnetic marker inside the socket. The small magnetic disc serves as a phantomic magnetic marker.
4) Marker the location of the phantomic marker before taking off it.
5) Move the sensor block close the marked location until the reading of the sensor indicates that the magnetic marker is in the center of the sensor's measurement range.
6) Rotate the sensor block around the z-axis (as shown in HU 8A) without changing its reading until its orientation is aligned with the proximal-distal direction.

This exemplary procedure allows for the magnet to be tracked when the magnet moves proximally up to 12.7 mm (much larger than the expected pistoning motion) and distally up to 6 mm (in the case of a shrinking residuum) from its current position. Considering the range of measurement, daily sensor location calibration is not expected to be necessary. However, if location readjustment is needed, the calibration procedure may be easily performed by a caregiver.

Testing of Exemplary Embodiments

A socket system according to the principles illustrated in FIG. 5 was tested via bench test. In the test, a permanent permeant magnetic disk was attached on the liner's external surface as an active magnetic marker. A magnetic measurement block was aligned with the marker and attached on the outside of the socket. A coordinate system was also defined to describe the motion of the marker. The change of distance between the marker and the measurement block along x axis (distal-proximal direction) indicated the pistoning that to be tracked. We assumed that the rotation of the magnet was ignorable because the magnet translated a very small distance on the internal surface of the socket, which was quite flat.

Pistoning is defined for purposes herein as the relative displacement between one point on the liner, which was indicated by the magnetic marker, and the prosthetic socket. This definition was chosen for its convenience of application and aligned with similar studies. The related efforts included: simulation study, electronic design and manufacturing, mechanical fixture construction, and software programming. The developed prototype was tested on the testing bed designed for this project and later evaluated on amputee patients.

Simulation Study

A pilot study based on numerical simulation using an open source software: Finite Element Method Magnetics (FEMM) was conducted. Based on the selected magnetic sensor and magnetic marker, output of each magnetic sensor when the magnetic marker was located at various locations within the measurement range could be calculated. The pilot study was designed to 1) understand the performance of a single sensor element, and 2) develop and validate auto compensation capability to eliminate influence of motions, which is not along distal-proximal direction.

Results of the pilot study indicated that the sensor output and motion between magnetic sensor and magnet along the distal-proximal direction were linear related; and 2) influence of motions along the other two directions either was ignorable or could be compensated.

Performance of Single Sensor Element

We identified relationship between sensor reading and relative displacement between the magnet and the sensor based on FEMM simulation results. Although this software only provides 2D magnetic field simulation, we could interpret the whole 3D space magnetic field through coordinate translation, because the magnet is axisymmetric. By putting the magnetic disks at the original (O), we calculated the magnetic angle sensor, S1, reading at any locations ($x_m$, $y_m$, $z_m$) to evaluate the performance of the proposed SSMS. The results of this study indicated that 1) marker movement along the y axis (as shown in the FIG. 5) does not affect pistoning (movement along the x axis) measurement; 2) marker movement along the z axis generate unexpected noise to the pistoning measurement and had to be compensated.

Figure 9A:
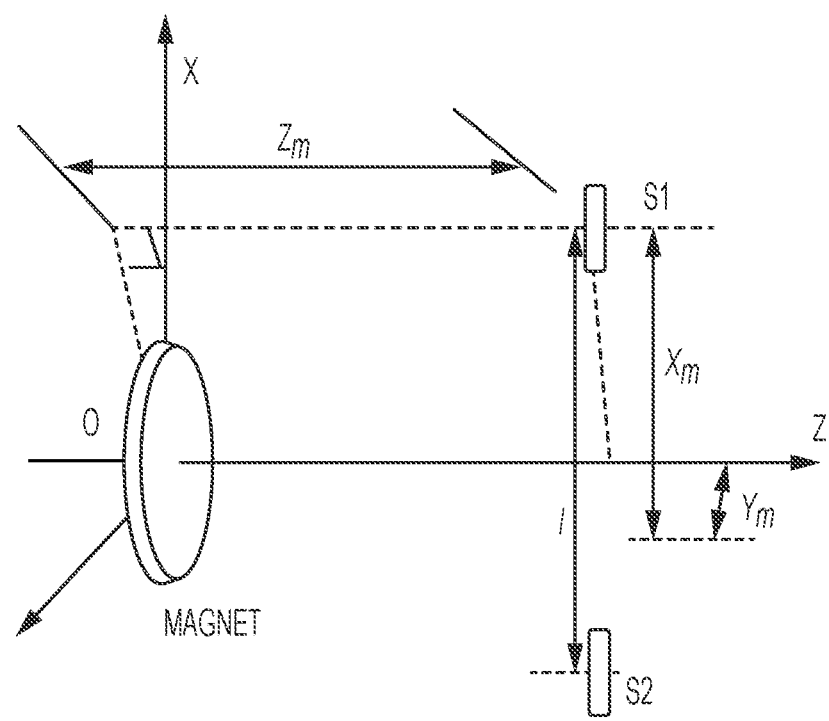
FIG. 9A illustrates sensor location and related coordinate system used in the simulation study.
Figure 9B:
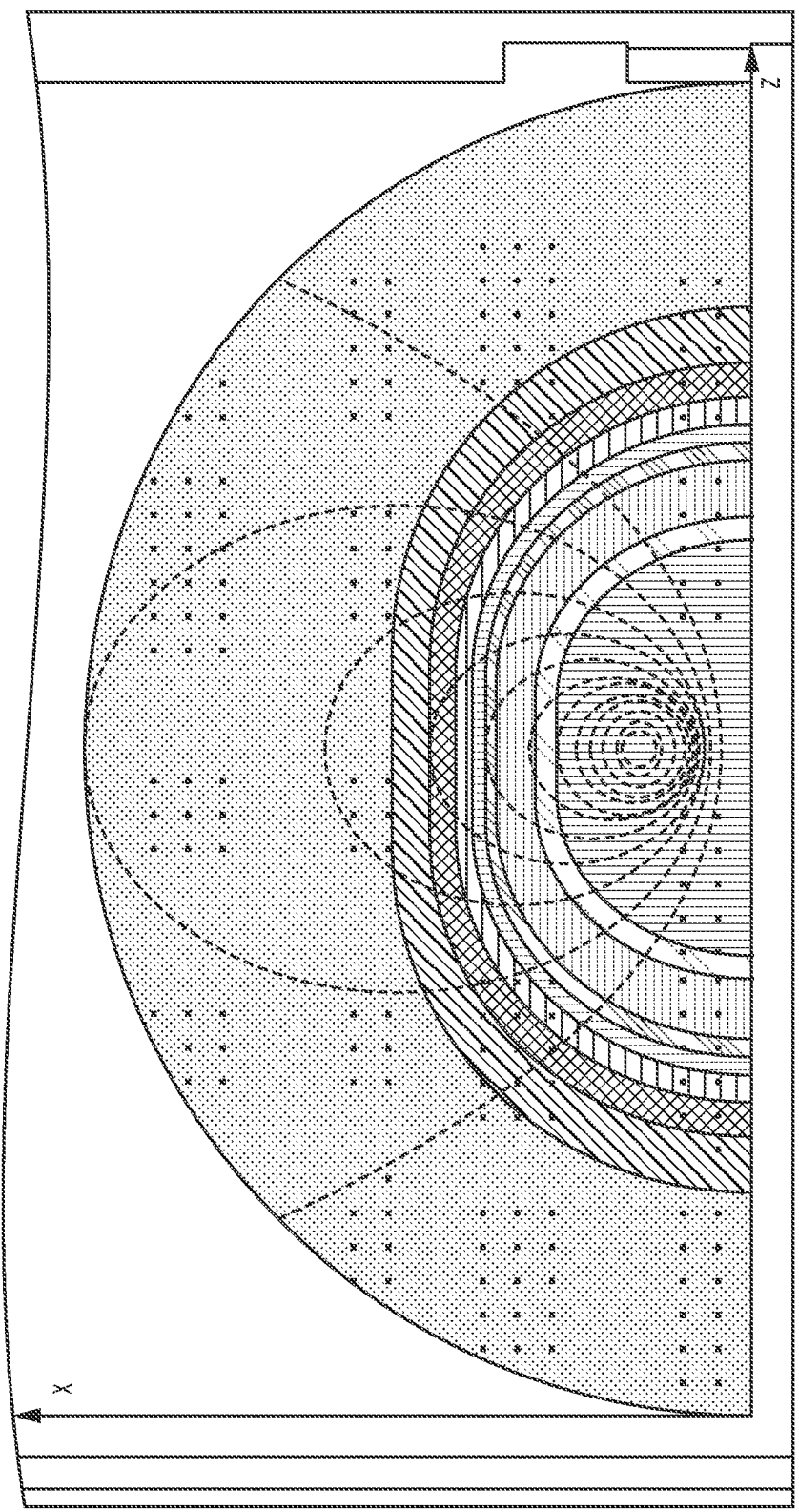
FIG. 9B shows the distribution of magnetic field around the magnetic marker based on finite element analysis.

FIG. 9A illustrates sensor location and related coordinate system, where S1 and S2 are magnetic angle sensors; and simulation of the magnetic field of a magnetic disk (1 mm thickness with 5 mm diameter from N52).

Tops of the magnetic sensors were arranged along the xz plane shown in FIG. 9A. For each magnetic angle sensor, there is a sensitive surface, which is parallel with the top surface of the sensor element. A projection of the local magnetic field on this sensitive surface is compared with the reference magnetic field, which is predefined in the sensitive surface, and relative angle between the projection component and the reference magnetic field is use as the output of the sensor. When the magnet is moving along the x axis, the output angle is a linear function of the distance between the sensor and the magnet.

Figure 10B:
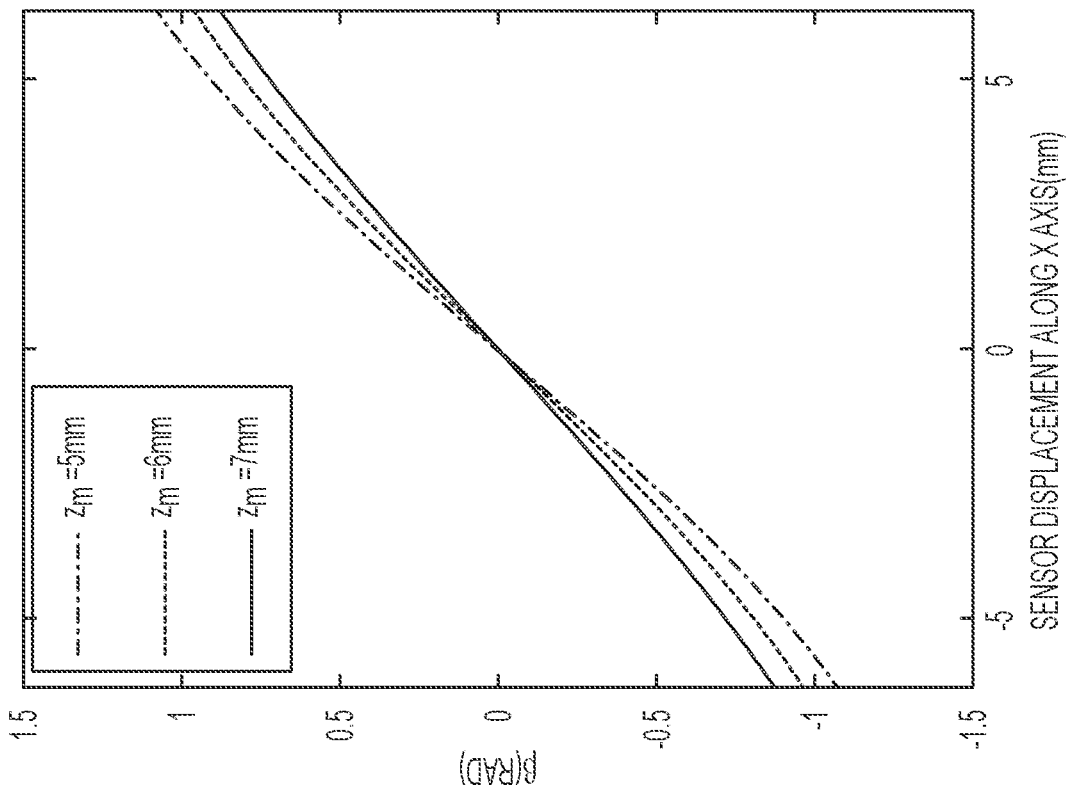
FIGS. 10A and 10B show SSMS measurement based on simulation.
Figure 10A:
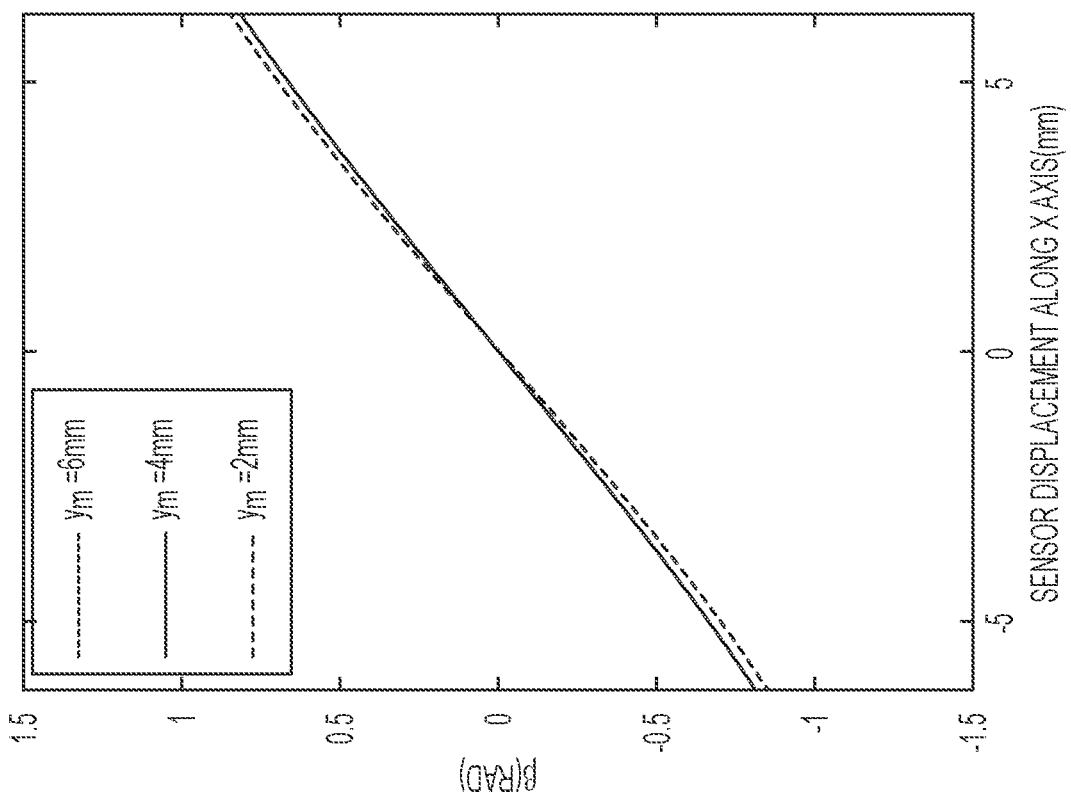

FIGS. 10A and 10B show SSMS measurement based on simulation. FIG. 10A with $z_m$=6.8 mm and FIG. ZB with $y_m$=3.5 mm. Based on the sensor orientation mentioned in FIGS. 10A and 10B, we calculated the angle between the component of the magnetic field projection in the xz plan and a reference magnetic field in the same plan which was aligned with x axis. To understand the performance of the SSMS under motion along different axis, we conducted two types of numerical study. First, we moved the magnetic sensor along x axis with fixed $z_{m0}$ and different $y_m$. Secondly, we moved the magnetic sensor along x axis with fixed $y_{m0}$ and different $z_m$. The constant value $z_{m0}$=6.8 mm is sum of average thickness of the socket (3.8 mm), average thickness of 3 ply socks (1.5 mm), and 1.5 mm for the distance between measurement center of the sensor element and the socket surface; $y_{m0}$=3 mm is half of the maximum expected displacement on the y direction. FIG. 10A shows that the β angle has a good linear relationship with the sensor displacement along x axis with a fixed $z_m$ and is not sensitive the displacement along the y axis, but the displacement along z axis does cause errors in the SSMS as shown in FIG. 10B.

Electronic Design of the SSMS

A prototype of the SSMS was developed based on AAT003-10E (NVE Corporation, MN, USA), a magnetic sensor, which outputs the angle between external magnetic field and a predefined reference direction in its sensitive surface. Comparable systems could also be built based on other similar sensor elements.

Figure 11:
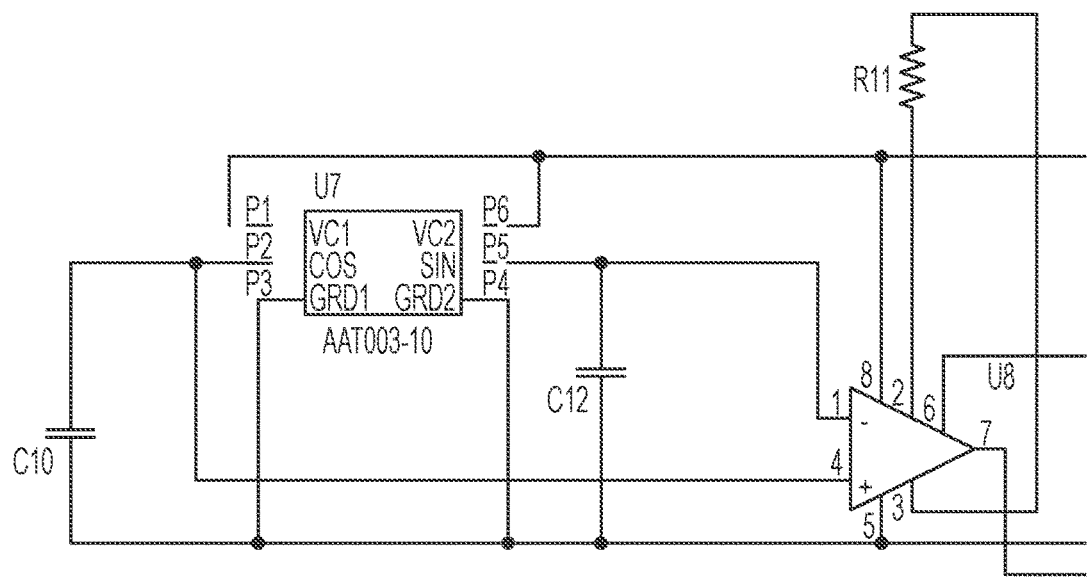
FIG. 11 shows a single sensor setup.

To reach larger signal amplitude, more precision, and less temperature dependence, a differential amplification approach was adopted for this system. The exemplary single sensor setup is shown in the FIG. 11. Exemplary values of C10 and C12 are 100 pF and an exemplary value of R11 is 33K. Based on previous simulation results, it was reasonable to assume that there existed a linear relation between magnetic field orientation and the distance between the sensor element and the magnetic marker when the marker was close to the sensor element. The reading from the single sensor element should be:

$$v_i = A_i \sin\left(\frac{x_i}{d_i} - \frac{\pi}{4}\right) + B_i \qquad \text{Eq. (1)}$$

where i indicates the label of each sensor element; the voltage reading for ith sensor element; $A_i$ and $B_i$ are constants, which were decided by the electronic components used to support the ith sensor element; was projection of the distance from the magnetic marker to the ith sensor element on the top surface of the magnetic marker; $d_i$ was a variable related to the distance between the sensor element and the top surface of the magnetic marker (z as shown in FIG. 9A). Here we assumed that the North Pole of the magnetic marker faced the sensor element and served as its top surface.

Because the measurement range of single sensor element was limited (around ±7 mm based on simulation results), multiple sensor elements were used to ensure that the measurement range of SSMS fully covered the potential movement region of the magnetic marker. So, an array setup was adopted with 4 sensor elements arrange in a row. This setup was selected based on our observation that the real pistoning amplitude was small for a well-fitted socket. Additional sensor elements may be needed in the future.

Two major modifications were made to ensure consistency among different sensor elements: 1) adding a REF3225 (Texas Instruments, TX) voltage reference to ensure the amplifier for each sensor element had the same reference voltage and 2) adding a REG113EA-5/250 (Texas Instruments, TX) voltage regulator to ensure that the signal readings were not affected by the small voltage change of the power sources (a situation, which was expected when batteries were used to provide power).

One key design parameter of the SSMS system was the distance between each sensor element. This parameter, l, directly affected: measurement range, measurement accuracy, cost, and software parameter selection. For a smaller l, we expected better measurement accuracy but smaller measurement range when the number of the sensor elements were fixed. For the initial prototype we chose to maximize the measurement accuracy by minimizing l=7 mm. Further reducing of this parameter would significantly increase the manufactural cost of the SSMS, which was also a major concern for the system design.

Figure 12A:
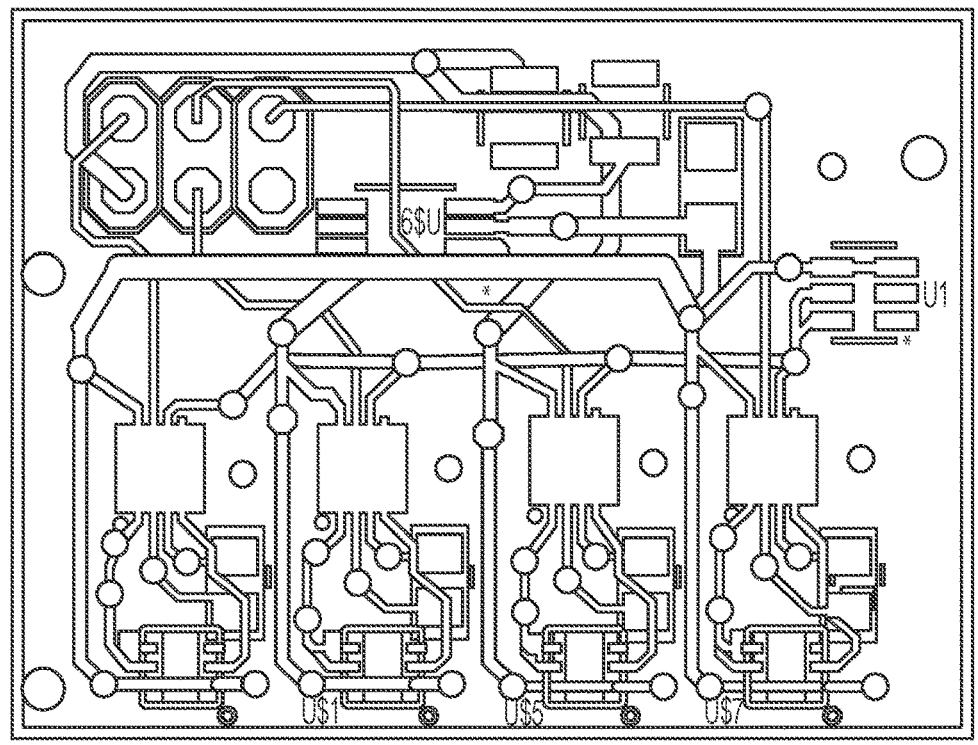
FIG. 12A shows an electronic circuit board design according to principles of the present disclosure.

FIG. 12A illustrates the PCB design of the constructed SSMS.

Physical Construction of the SSMS

Figure 12B:
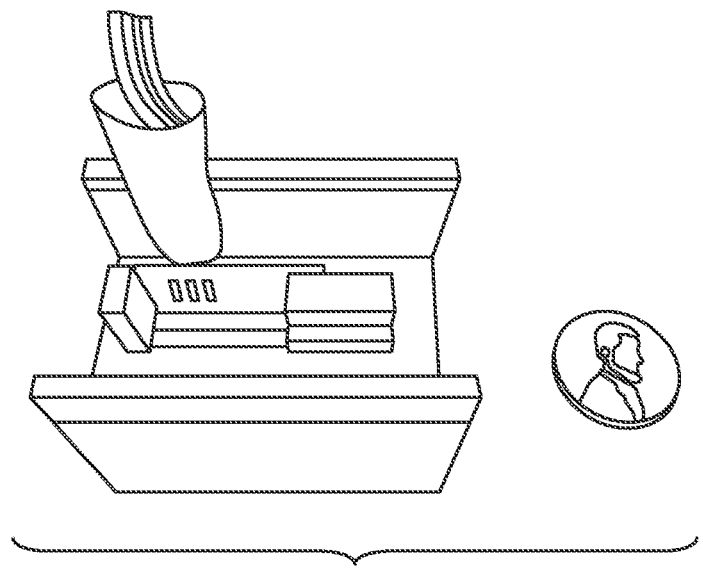
FIG. 12B illustrates the size of an assembled socket monitoring system prototype.

The manufacture of the SSMS included: manufacture of the electronic board and manufacture of the sensor box. The electronic board manufacture followed the standard procedure and the electronic elements were soldered on manually and through an overflow oven. The sensor box was made by assembling multiple plastic pieces, which were machined using a laser cutter. These pieces were permanently fixed together using super glue. The assembled SSMS prototype was shown in FIG. 12B.

SSMS Measurement Software Development

Figure 13:
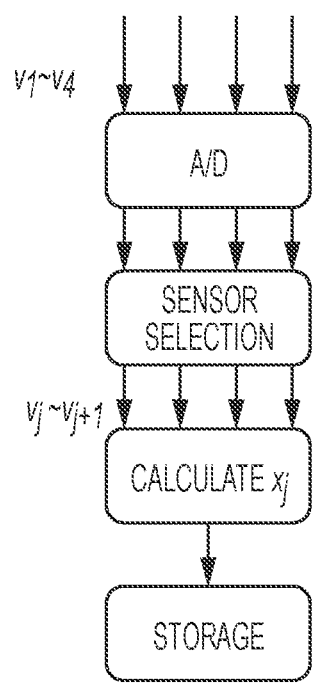
FIG. 13 illustrates a basic software structure according to principles described herein.

To take the advantages of the SSMS hardware, a special software was designed to enable continuous monitoring of the marker movement. The basic structure of the software was shown in FIG. 13.

As shown Eq. (1), measurement from a single sensor element, $v_i$ could not be used to calculate the $x_i$ directly due to the usually unknown $d_i$. To overcome this limitation, a dual sensor approach was adopted. Because we usually selected a relative flat surface on the socket to mount the sensor box, it is reasonable to assume that for given sensor element j and j+1, the corresponding $d_j$ and $d_{j+1}$ were identical. So the Eq. (1) could be applied to the sensor element j and j+1 as:

$$\begin{cases} v_j = A_j \sin\left(\frac{x_j}{d_j} - \frac{\pi}{4}\right) + B_j \\ v_{j+1} = A_{j+1} \sin\left(\frac{x_j + l}{d_{j+1}} - \frac{\pi}{4}\right) + B_{j+1} \end{cases} \qquad \text{Eq. (2)}$$

Because $A_j$, $A_{j+1}$, $B_j$, and $B_{j+1}$ could be identified through calibration and l=7 mm represented the distance between sensor elements, the Eq. 2 could be written as:

$$\begin{cases} x_j = \left(\mathrm{asin}((v_j - B_j)/A_j) + \frac{\pi}{4}\right) d_j \\ x_j + l = \left(\mathrm{asin}((v_{j+1} - B_{j+1})/A_{j+1}) + \frac{\pi}{4}\right) d_{j+1} \end{cases} \qquad \text{Eq. (3)}$$

Because $d_j=d_{j+1}$, only two unknown parameters existed in the Eq. (3) were $x_j$ and $d_j$. By solving the Eq. 3, the $x_j$ was calculated; then the $x_j$ was converted into the relative distance between the magnetic marker and the SSMS based on the location of sensor element j.

Based on our observation, there usually existed more than two sensor elements, of which readings could be used to calculate the relative distance between the magnetic marker and the SMSS system. The sensor selection was based on the measurement function Eq. (2) and the linear assumption between $x_i$ and the orientation of the magnetic field.

As shown in our previous simulation study, the linear relationship between the $x_i$ and the orientation of the magnetic field ($\theta$) would hold well when the sensor element was closed to the magnetic marker. So, the sensor elements, which were close to the magnetic marker should be selected. However, because the Eq. (1), the solution of $x_i$ was not unique when $$\frac{x_i}{d_i} < -\frac{\pi}{4}.$$

Figure 14:
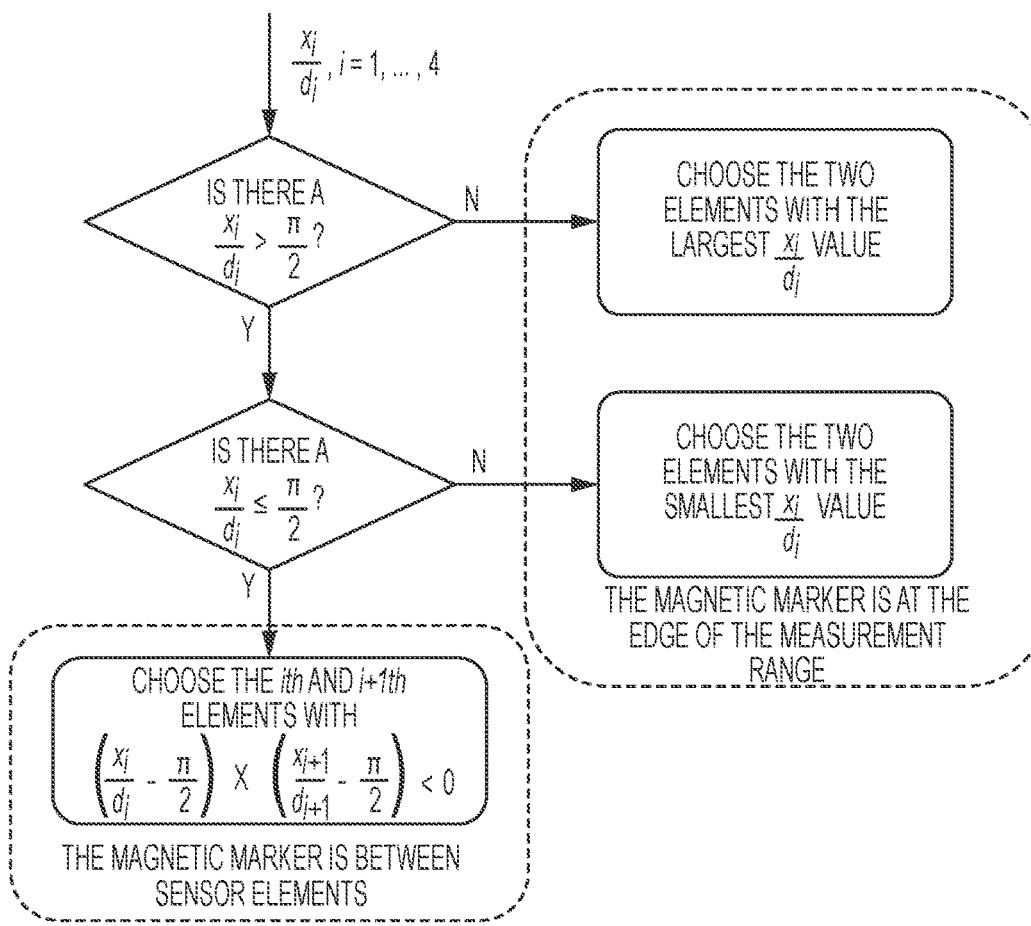
FIG. 14 is a flowchart illustrating sensor element selection.

Based on our initial testing results, $$\left|\frac{x_i}{d_i}\right| < \frac{\pi}{2}$$

when $|x_i|<2l$, we designed a sensor selection strategy, of which a flowchart was shown in the FIG. 14.

For this initial prototype, the measurement system was constructed based on a PC based DAQ system under the LabView environment. The measurement system was running at 200 Hz DAQ frequency and all collected data were stored in the hard drive for further analysis.

Testing Bed and Initial Evaluation Results

Figure 15:
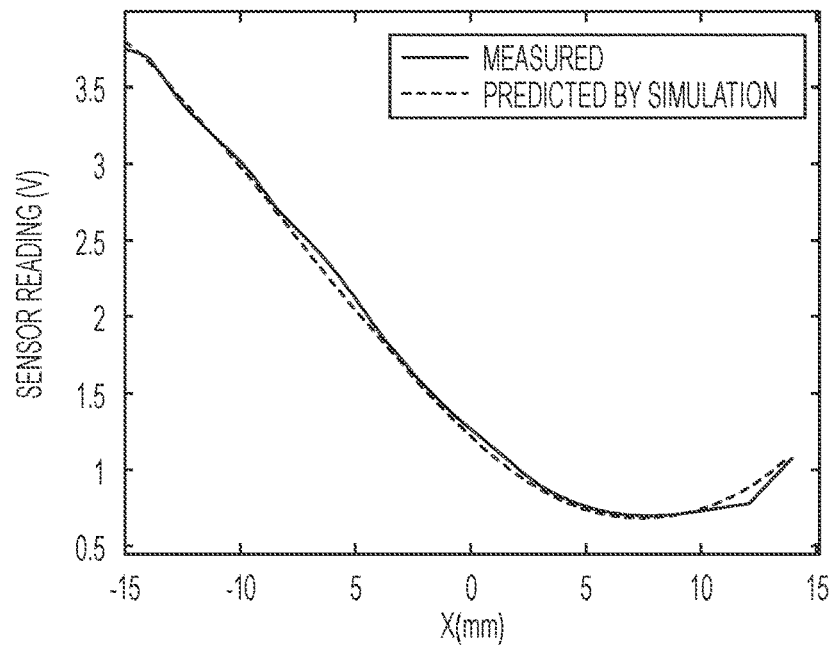
FIG. 15 shows raw data from a single magnetic element when the SSMS moved along a paralleled rail.

To calibrate the SSMS and evaluate its performance, a calibration platform was constructed as shown in FIG. 8B. As shown in the picture, the magnet marker (a white plate) was fixed in the middle. The SSMS was mounted on the top rail with its sensor array aligned with the direction defined by the paralleled rails. The performance of the SSMS was evaluated in the test bed. The signal reading from one sensor element, when the SSMS moved along the paralleled rails, was shown in FIG. 15. The shape fitted with the results predicted by our model and aligned with Eq. 1 very well. In this case, x was defined as projection of the distance from the sensor element to the magnetic marker on the top surface of the magnetic marker, so the Eq. (1) was rewritten as:

$$v = A\sin\left(\frac{x}{d} + \frac{\pi}{4}\right) + B \quad \text{Eq. (4)}$$

with A was negative and d was a constant. Similar data sets also provided needed data to estimate the constants $A_i$ and $B_i$ for each element through least square fitting.

Evaluate the pistoning of transtibial amputees during locomotion

To apply the developed SSMS into clinical application, one critical question was where we should conduct the pistoning level monitoring on the residual limb because it is well expected that the pistoning level is different from point to point.

To ensure that the SSMS could generate meaningful information, we expected that the measurement point should meet the following criteria:

(1) Pistoning level was dominated by the movement along the distal proximal direction, which was monitored by the SSMS.
(2) Pistoning level was sensitive to change of residual limb volume.

To address this question, we developed a Magneto-Optic Hybrid pistoning monitoring approach, which permitted us to monitor the level of pistoning during dynamic walking. Then we conducted experimental study to compare the pistoning level on different locations on human subjects.

Methods

To overcome the above limitations, we developed a pistoning evaluation procedure using an electromagnetic based motion capture system in conjugation with an optical motion capture system. This pistoning evaluation approach took advantages of the two motion capture systems. The probe of the electromagnetic system is small (see FIG. 16) and can be mounted on the liner inside the socket. However, the measurement range of these small probes was limited and cannot be used to monitor a broad range of motion. The optical system had a large measurement range with high accuracy but cannot be used to monitor anything inside the socket. Here we used the magnetic system to monitor the movement of the liner and the optical system to monitor the movement of the socket. By calibrating the two systems, we could calculate the pistoning level, which is defined as the relative displacement between the socket and the liner.

Experimental Setup

Figure 16:
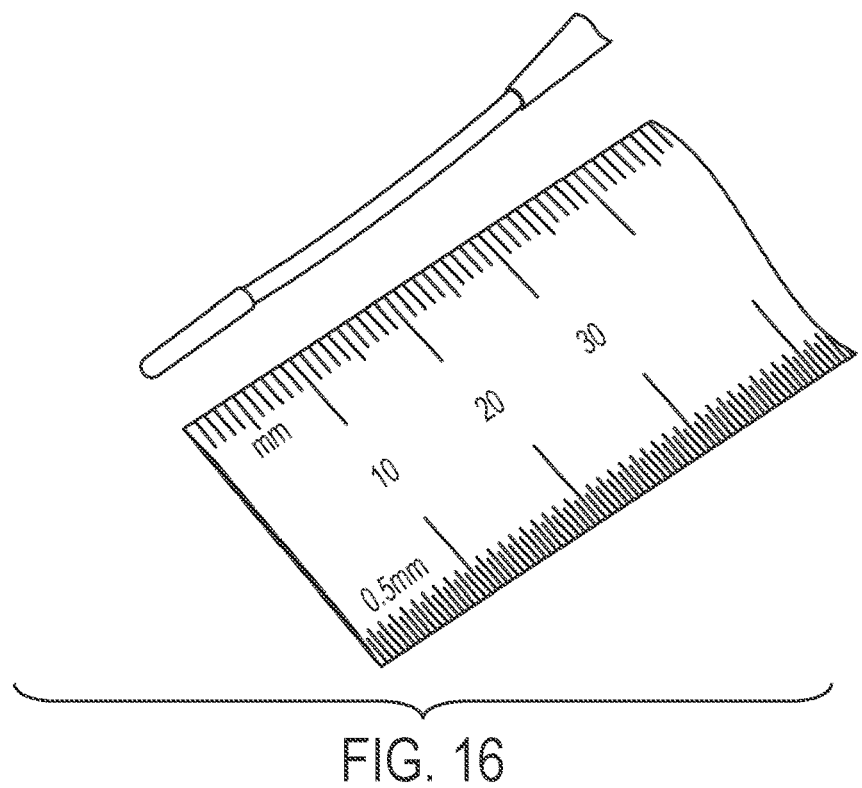
FIG. 16 illustrates trakSTAR sensor element used in the study described herein.

Two motion capture systems were adopted: 1) an 8-camera motion capture system (10 markers, 100 Hz, VICON, Oxford, UK) and 2) and a six degree of freedom electromagnetic tracker designed for short-range motion tracking applications (3DGuidance trakSTAR, Ascension Technology Corp., Burlington, Vt.). The trakSTAR system consists of a short-range dipole (3-coil) transmitter with a translation range of ±45 cm in any direction. A small sensor probe (Model 180 with 2 mm diameter and 10 mm length) was selected to reduce the risk caused by the sensor element to the subjects' skin (see FIG. 16). FIG. 16 illustrates a trakSTAR sensor element used in the study.

Figure 17:
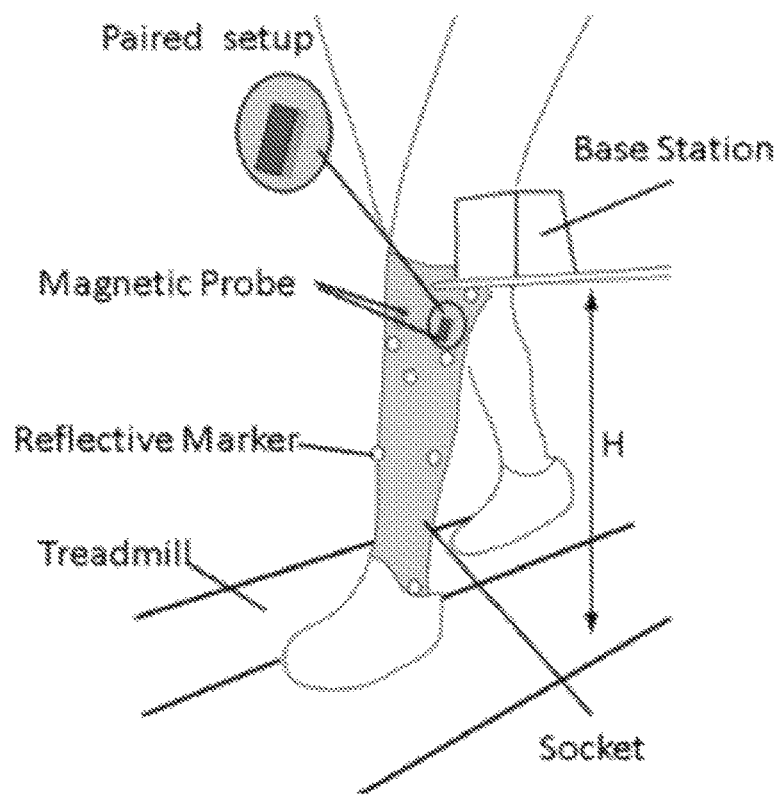
FIG. 17 illustrates a socket configuration with the markers attached to it.

The measurement setup was constructed for a treadmill walking task. Because of the relatively small measurement range of the magnetic motion capture system, it was challenging to cover one full gait cycle in a level ground walking task. The whole experimental setup was demonstrated in FIG. 17. FIG. 17: The socket configuration with the markers attached to it. H is the height of the base station. The magnetic probes were placed on the socket surface and on the liner. The long axes of the magnetic probes were aligned along the proximal-distal direction in a paired setup (a probe on the socket and another probe on the liner located as close as possible to the socket probe). Five reflective markers were mounted on the socket around the magnetic probes to construct a rigid body model later, and additionally four markers were placed at the medial and lateral sides of the knee and ankle centers. The base station of the magnetic motion capture system was mounted on a separated structure, which was fixed during the test.

Figure 18:
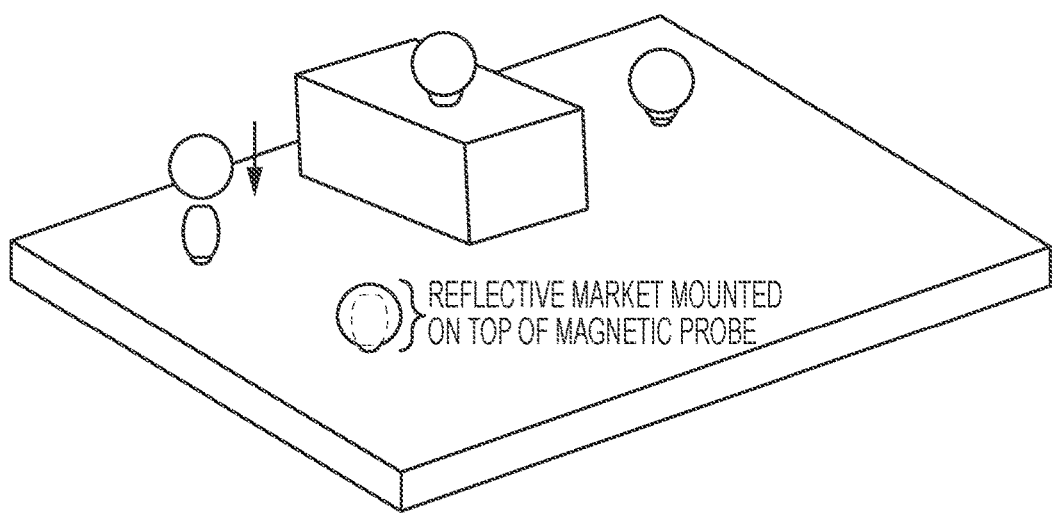
FIG. 18 illustrates a platform used for calibrating the two motion capture systems.

The calibration between the two motion capture systems was conducted using a custom-built platform as shown in FIG. 18. FIG. 18: shows the platform used for calibrating the two motion capture systems. Four optical markers were mounted on top of four magnetic probes such that the probes were at the center of the optical markers. The magnetic probes were mounted on a platform via small holes on the platform; and reflective markers were added on top of the magnetic probes, so that the magnetic sensors were at the center of the reflective markers. The locations of the probes and the markers were recorded by the two motion capture systems, which were synchronized. The single value decomposition (SVD) based best-fitting rigid transformation was used to calculate the translation matrix related with the two motion capture systems respectively. During the calibration, the heights of the calibration platform and the base station were identical.

Experimental Design

One of the known issues with magnetic motion capture systems is their vulnerability to external magnetic fields. Both the motor of the treadmill and the force plates embedded in the treadmill had the potential to generate disturbance on the magnetic motion capture system. Two reasons made us believe that our magnetic motion capture system could provide accurate readings: 1) we only planned to measure the pistoning on the proximal side of the shank, so the base station could be mounted quite far away from the treadmill; 2) the selected magnetic system had a very small measurement range which could prevent the influence of magnetic disturbance from the treadmill. However, it was still necessary to validate the measurement accuracy of the systems before the readings could be relied upon.

Two experiments were conducted to evaluate the capability of the Magneto-Optic Hybrid systems: 1) a repeated calibration test to evaluate the impact of the treadmill on the sensor reading; and 2) a dynamic walking test to check its general performance.

The repeated calibration test was conducted by calibration the two systems with different H. After the transformation matrix was calculated, the location of the magnetic probes was calculated in the coordinate system defined by the Vicon system. Small error between the two motion capture systems was a good indicator of the magnetic motion capture system's ability to generate accurate readings at this height.

The dynamic walking tests were conducted on a human subject. With an experimental protocol approved by the Institutional Review Board of the University of North Carolina at Chapel Hill and informed consent, one male unilateral amputee (117 kg, 180 cm) participated in the study. The subject used a roll-on-liner and a pin-lock suspension system and was capable of walking on a treadmill without relying on rails. After a static measurement, which was used to build the rigid body model of the socket, the subject was instructed to walk on the treadmill with a self-selected walking speed. The motion of the residual limb and the socket were recorded using the two motion capture systems.

To evaluate the performance of the magnetic motion capture system, we tracked the trajectory of the magnetic probe, which was attached to the socket using the two motion capture systems. Based on the static measurement, we defined a virtual point on the socket at the location of the magnetic probe. Then we calculated the trajectory of the virtual point based on the rigid body model defined by the reflective markers on the socket. The trajectory of the virtual marker was compared to the measurements captured by the magnetic motion capture system. Overlap of the two trajectories indicated reliable measurements from the magnetic motion capture system.

Results

Calibration Accuracy

Figure 19:
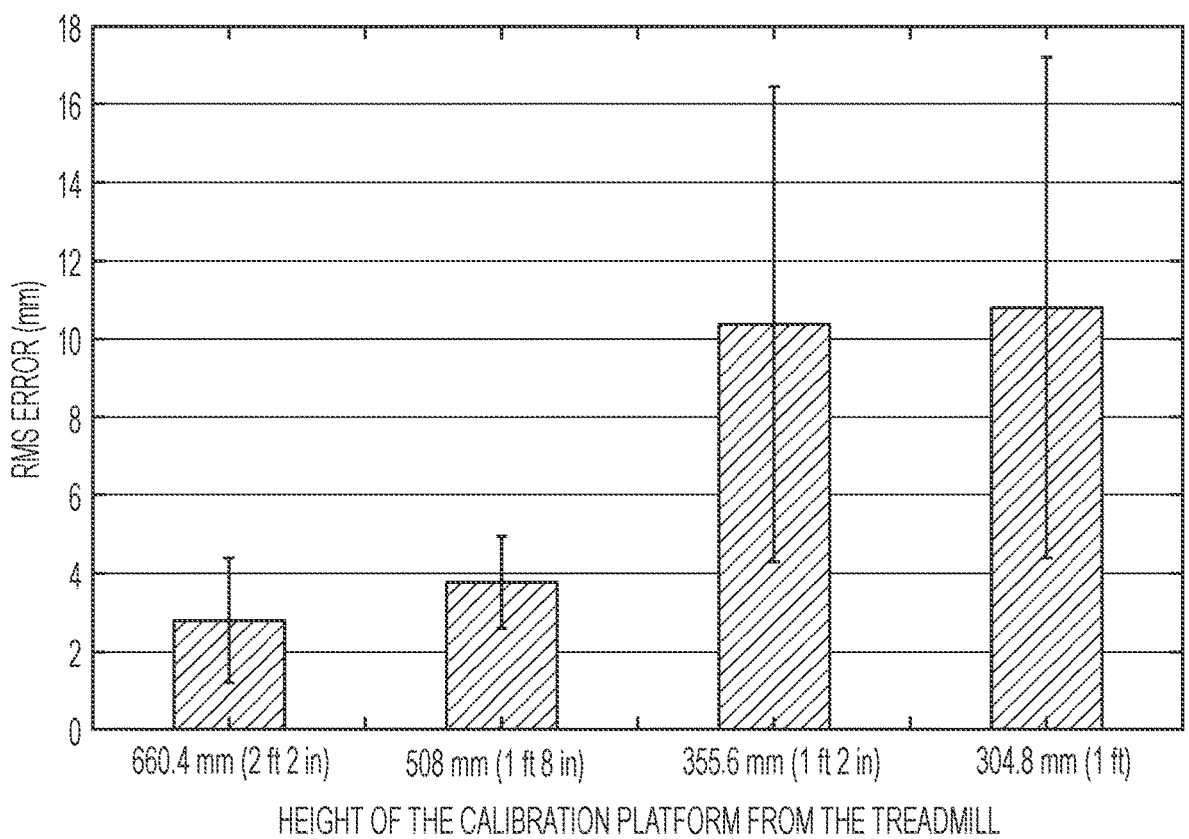
FIG. 19: Height of the calibration platform from the treadmill versus the error associated with the calibration.

FIG. 19 shows the height of the calibration platform from the treadmill versus the error associated with the calibration. FIG. 19 demonstrated the relationship between the calibrations errors, root mean square (RMS), and height of the base station. When the base station was higher than 660.4 millimeters (2 feet 2 inches), the calibration error was close to the defined measurement accuracy of the trakSTAR system (~2 mm). Based on this result, we chose to place the trakSTAR system at a height of 609.6 millimeters (2 feet) from the treadmill to ensure adequate data capture area while reducing the disturbance associated with the treadmill.

Tracking Performance

Figure 20:
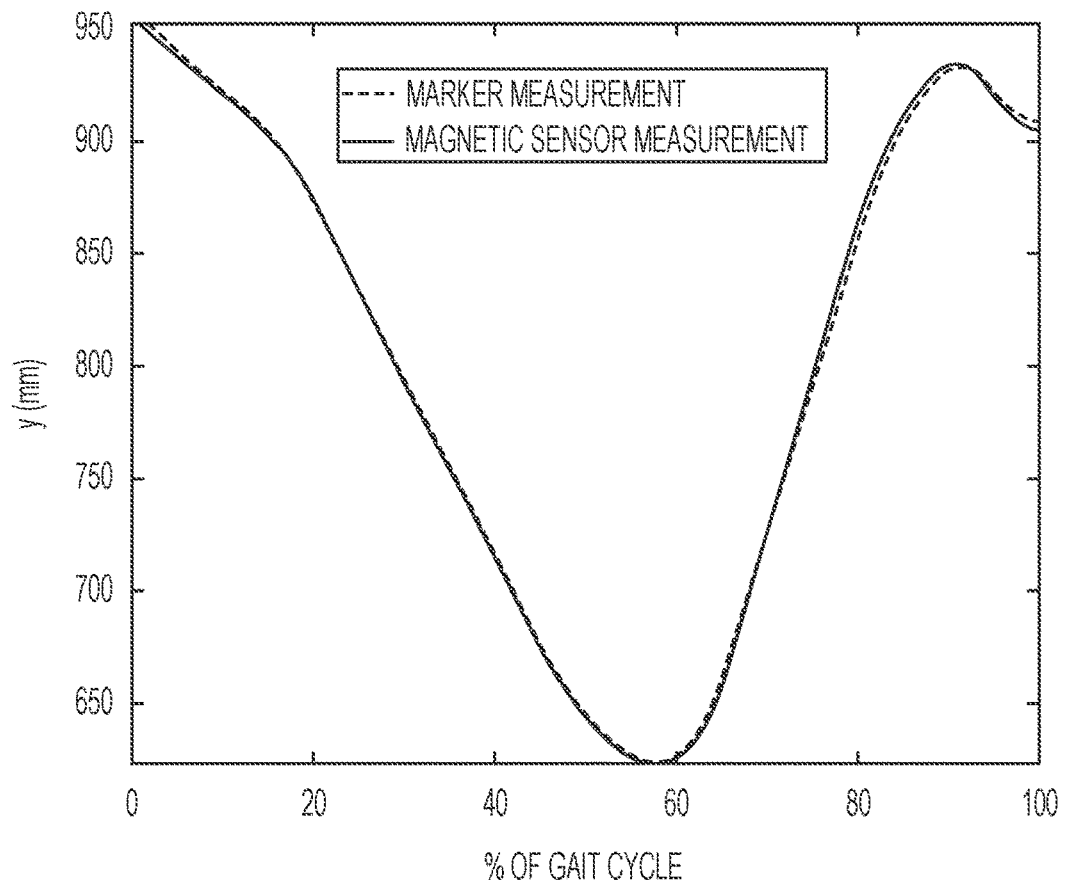
FIG. 20: Trajectory of the magnetic probe using the trakSTAR system's measurement and trajectory of the magnetic probe defined using a virtual point on the socket.

FIG. 20 shows the trajectory of the magnetic probe using the trakSTAR system's measurement and trajectory of the magnetic probe defined using a virtual point on the socket FIG. 20 showed the trajectory tracking performance in distal-proximal direction during walking. As can be seen, the two trajectories overlapped each other reasonable well during most of the gait cycle, which indicated that the trakSTAR system can provide a reliable measurement in the current setup.

Local Linear Model Based Dynamic Calibration

Background

Although the Magneto-Optic Hybrid pistoning monitoring system demonstrated potential to monitor the dynamic pistoning, it was still necessary to address the errors related to the magnetic motion capture system. The standard approach to limit this error was to conduct an extensive calibration in the measurement range of the magnetic motion capture system and generate a lookup table. Because the error of the magnetic motion capture system was decided by the location of the magnetic probe, the real error can be estimated using the lookup table.

Any additional metal pieces could introduce errors in the reading of the magnetic motion capture system and it was known that the calibration results changed if there were any changes in the environmental magnetic field. So a new calibration was recommended every time before a test. Practically, it was a challenge to conduct this calibration procedure due to the following factors: 1) the repeatability of the calibration procedure is not guaranteed and 2) it can be a time-consuming procedure to cover the full measurement range.

In this session, all errors were referenced to the difference between measurements from the magnetic motion capture system and the ones from the optical motion capture system. The later one was usually regarded as accurate.

Method

The fact, which our pistoning monitoring approach was under continuous monitoring of two motion capture systems, provided a unique opportunity to adopt a dynamical calibration procedure. The dynamical procedure was realized by modifying the setup shown in FIG. 17 based on the following procedure:

(1) Attach one magnetic sensor tube on the surface of the socket as the reference.

(2) Encourage the subject to adjust his/her relative position on the treadmill, so the reference point could cover large area in the measurement space (3) Calculate the error of the reference point based on the rigid body model of the socket constructed from optical markers.

(4) Build local linear models to predict errors for any new observation from the magnetic motion capture system.

(5) Improve the accuracy of the magnetic motion capture system by removing the calculated error.

Local Linear Model

Because the error related to magnetic motion capture system was a function of the location: $[x_e, y_e, z_e] = f(x, y, z)$, where $x_e$, $y_e$, $z_e$ are the error measured at the location x, y, z. Although $f$ was unknown function, it was known that this function was continuous in space. So the function $f$ can be approximated by a linear model:

$$\begin{pmatrix} x_e \\ y_e \\ z_e \end{pmatrix} = A \begin{pmatrix} x \\ y \\ z \end{pmatrix} + b, \qquad \text{Eq. (5)}$$

where A was a 3×3 matrix and b was a 3×1 vector. This approximation would be held in a small space around the point (x, y, z). For any measurement point $(x_m, y_m, z_m)$, the related measurement error could be calculated directly if related $A_m$ and $b_m$ are available.

Because it was reasonable to assume that the linear model based on $A_m$ and $b_m$ was accurate in a small area around the point $(x_m, y_m, z_m)$, we looking for nearest neighbors of the point $(x_m, y_m, z_m)$ among measured coordinates of the reference point, of which the measurement errors were available. Based on the location and measurement errors of these neighbors, $\overline{A_m}$ and $\overline{b_m}$ was estimated through least-square fitting. Then the measurement error at point $(x_m, y_m, z_m)$ was estimated using Eq. (5) by replacing the $A_m$ and $b_m$ with $\overline{A_m}$ and $\overline{b_m}$ respectively.

Results

In a setup like the one described in the previous session, data from an amputee subject were reprocessed to understand the performance of the local linear model (LLM) based dynamical calibration and compensation procedure.

Figure 21:
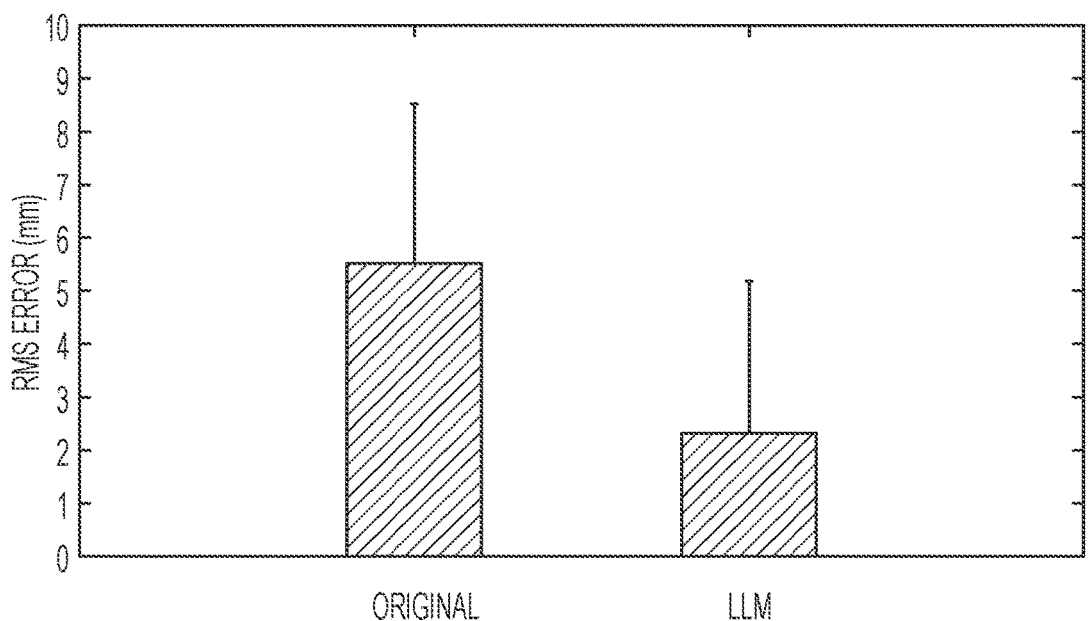
FIG. 21: the root mean square (RMS) error of the magnetic motion capture system.

The impact of the LLM based dynamical calibration and compensation procedure on the measurement accuracy was shown in FIG. 21. FIG. 21 shows the route mean square (RMS) error of the magnetic motion capture system. The route square error of the magnetic motion capture system dropped from 5 mm to 2 mm after the introducing the LLM based dynamical calibration procedure.

Identify Locations, which can be Used for Pistoning Monitoring

Based on the protocol approved by IRB at UNC-Chapel Hill, we recruited three unilateral amputee subjects with unilateral amputation. By comparing the pistoning level at different measurement points before and after a 7 minute walking trial (a standard procedure to trigger residual limb volume change), we could identify the locations, at which the pistoning level was sensitive to volume of the residual limb. The developed Magneto-Optic Hybrid pistoning monitoring system was used to monitor the dynamical pistoning.

Subjects

All of the subjects had been using their current socket for more than six months. All of them used a pin-locker suspension system and could walk on a treadmill without holding the rail consistently. Before conducting any tests, these subjects were given written consents. All three subjects were male with average height 178 cm and average weight 83 kg. All the amputations were caused by trauma.

Experimental Procedure

The whole experimental procedure included three steps: touch sensitivity test, sensor mounting, and 7 minutes test with pistoning monitoring.

The touch sensitivity evaluation followed standard monofilament testing, which is used to identify the patient's capability to detect dangerous pressure concentration on skin. Here we surveyed touch sensitivity of subjects' residual limb, especially around the area, where the magnetic sensor tubes would be mounted. This procedure ensured that the patient could detect abnormal pressure in these areas and stop the experimental procedure if it was necessary.

Sensor tube mounting was guided by several basic understandings of the interface between the residual limb and prosthetic socket.

(1) The pistoning monitoring sensor should be in the pressure tolerance areas on the residual limb.

(2) The sensor could not be on the lateral medial surfaces of the socket to avoid the chance of interference between the sensor box and the contralateral leg and external obstacles.

(3) The sensor should be mounted close to the top of the socket because the pin-locker suspension system should fix the distal end of the liner with the socket rigidly.

Figure 22:
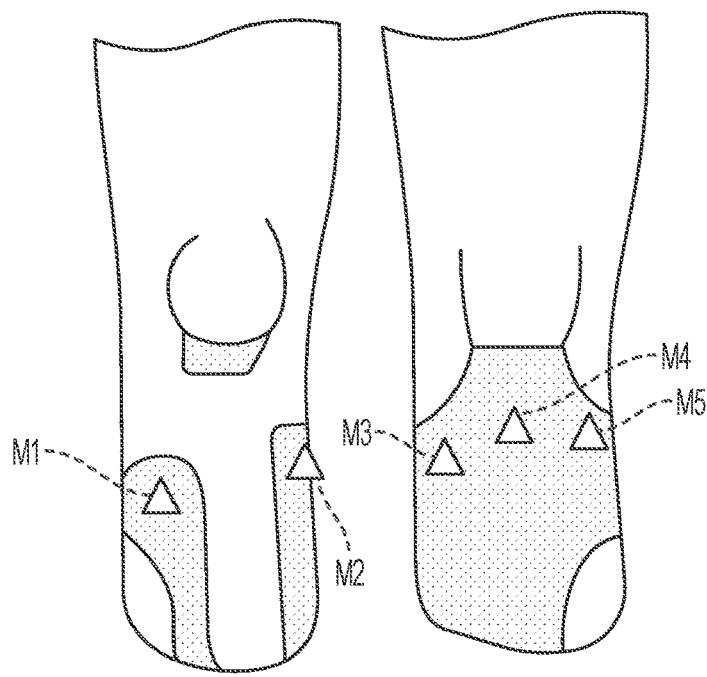
FIG. 22: Potential locations for magnets on the residuum.

FIG. 22 shows potential locations for magnets on the residuum. The gray area was pressure tolerance area. Potential measurement points were shown in triangles (M1 to M5) based on these criteria, M1-M5 (see FIG. 22) were identified as the initial measurement points. Among them, similar readings were expected for M3 and M5, and the curvature of the socket is usually high at the location of M5, which makes mounting sensor box a challenging task. So, the M1-M3 were further evaluated.

After all magnetic sensor tubes and reflected markers were mounted, the subjects were rested without socket for 10 minutes and started a 7 minutes walking trial at self-selected walking speed on a split treadmill with force plate embedded. The procedure was monitored by two motion capture systems and was participated in three sections. The first section and the third section lasted 30 seconds each and were assigned for pistoning monitoring. The subjects were instructed to walk in an area, where the sensor quality of the magnetic motion capture system was optimized. The second sections were used to collect dynamical calibration data, when the subjects were instructed to walk in a larger range on the treadmill to ensure that the reference points could cover a large part of the measurement range of the magnetic motion capture system.

Results

Figure 23:
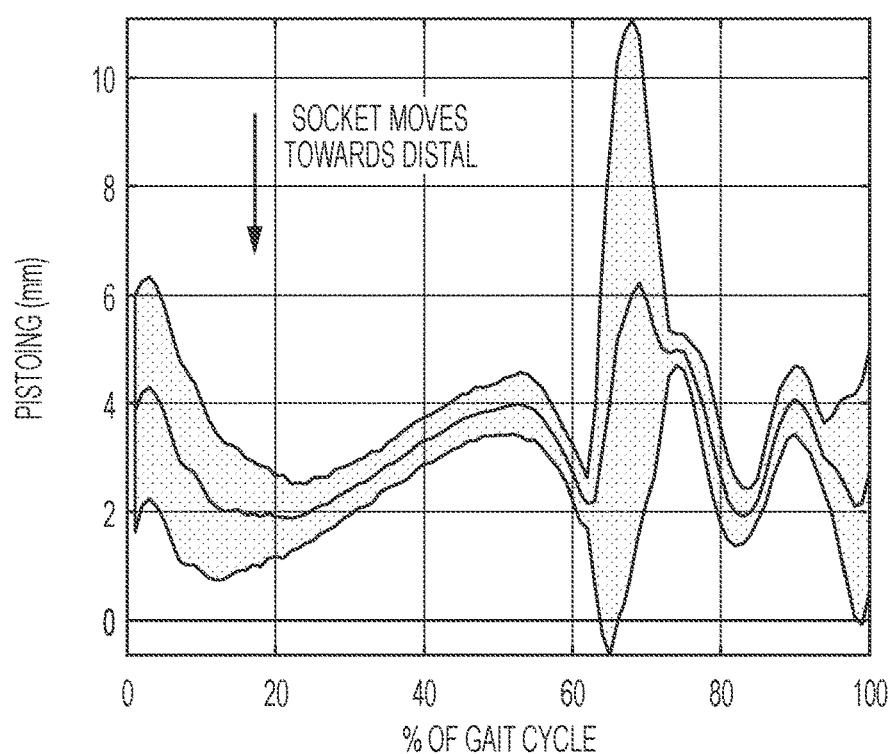
FIG. 23: Typical pistoning movement measured on an amputee subject.

FIG. 23 shows typical pistoning movement measured on an amputee subject. The solid black line indicated the mean value of the measured pistoning and the shadow showed the standard deviation based on 20 steps. Data was collected at M2. The amplitude of the pistoning was quite small. Due to the not so perfect synchronization of the two motion capture systems and the impact load during the heel strike and toe off procedure, large variation was observed at the heel strike and toe off when impact load happened.

The measured pistoning amplitudes, which were defined by the range of measured pistoning in each gait cycle, from all three subjects and three locations were very small (2.7 mm-4.4 mm), which were treated as acceptable for prosthetists. The pistoning amplitude did not change too much between the measurements in the first and third sessions. However, the average pistoning level, which was defined as the average pistoning reading in each gait cycle, changes average 2.2 mm among three subjects among all three locations. Although no statistical significant difference was observed due to small number of subjects, the results indicated that it was possible to monitor the pistoning level based on average pistoning level in various areas on the residual limb.

Test the Developed SSMS Prototype on an Amputee Subject

To evaluate the performance of the SSMS, we tested it on an transtibial amputee, who was male at 24 years old 176 cm height and 92 kg weight with a sleeveless vacuum suspension system. His suspension setup made it possible to simulate both an effective suspension system and an ineffective suspension system by connecting and disconnecting the pipe, which connected the pump on the foot and the socket, respectively. This gave us the opportunity to change the test condition without taking off the socket and made it a perfect case to evaluate SSMS.

SSMS Monitoring

A magnetic disc with ¼ inch diameter and 2 mm thickness was used as the magnetic marker and mounted on the liner of the subject using electronic tape. After the subject put on his socket, we used a second magnetic disc as the phantomic marker to identify the location of the magnetic marker inside the socket. Guided by this information, we carefully mount the SSMS on by following the previous defined mounting procedure.

Piston Reading During Walking

Pistoning was monitored during two walking trials when the subject was walking at the self-selected speed. In the first trial, the pump system was set at normal working condition to maintain a good suction fit. At the beginning of the second trial, the vacuum pump was disabled, the air flew into the vacuum chamber freely, which has a similar effect when the residual limb shrinks.

Figure 24:
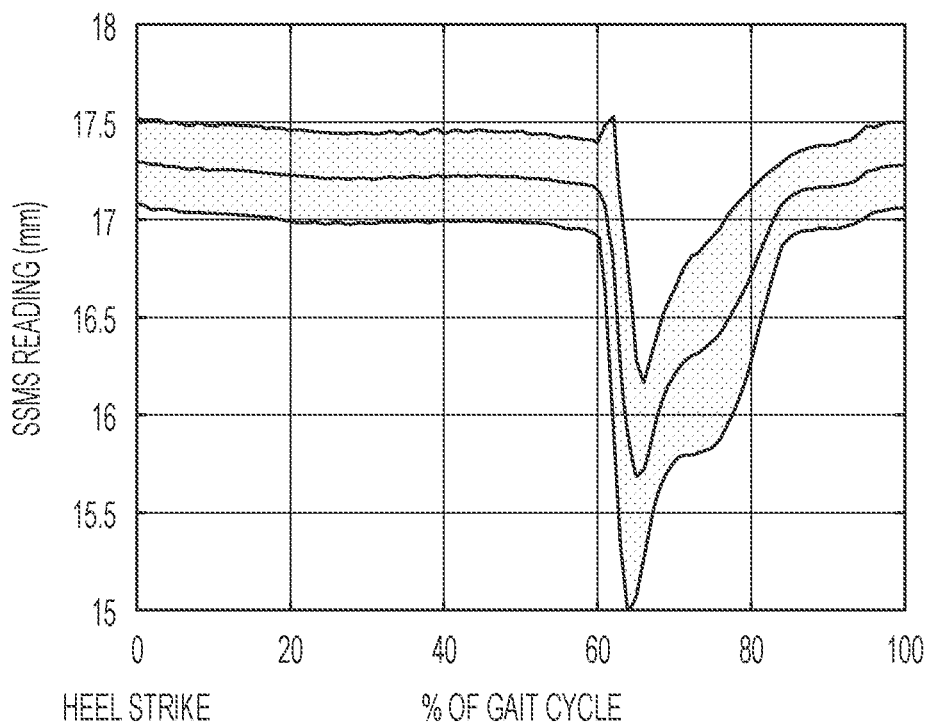
FIG. 24: The SSMS reading when the subject walked with good suspension system.

In both trials, the SSMS reading showed a similar trend in each step. FIG. 24 shows the SSMS reading when the subject walked with good suspension system. The gait cycle started with a heel strike. As shown in FIG. 24, the relative position of the residual limb and the socket maintained as a constant during the stance phase. The socket moved towards the distal end briefly during the push off and recovered during the swing phase.

Figure 25:
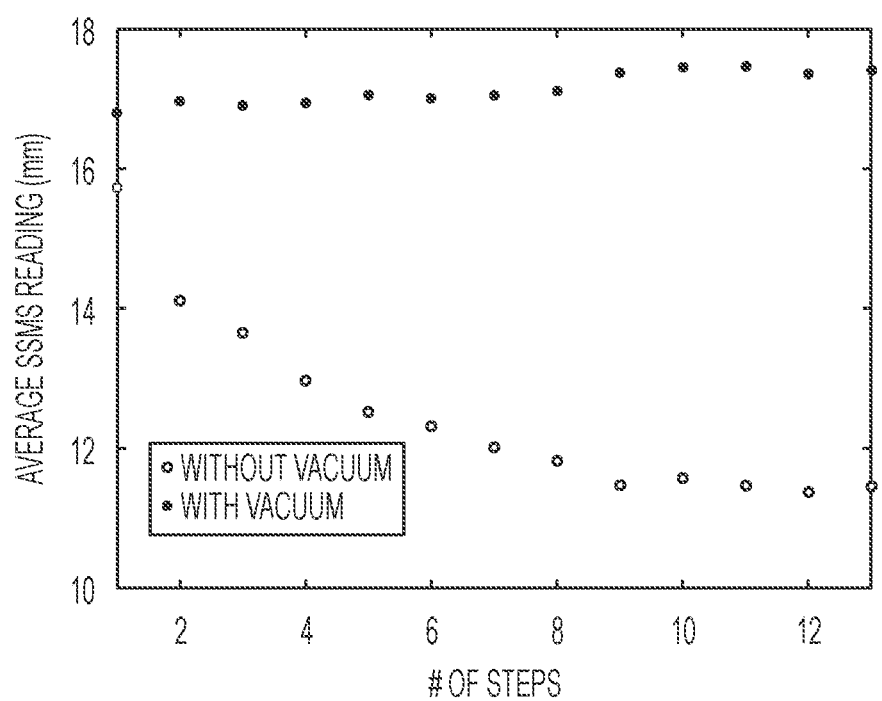
FIG. 25: The change of average pistoning level at two suspension situations.

Although the amplitude of pistoning for each gait cycle maintained relatively consistent during two trials, the average pistoning level demonstrated different trend in these two trials. FIG. 25 shows the change of average pistoning level at two suspension situations. As shown in FIG. 25, the average pistoning level maintained as a constant during walking when the pump was activated, but the socket quickly dropped off from the residual limb when the pump was deactivated, and the vacuum chamber was open.

This observation directly demonstrated the capacity of our SSMS to monitor the socket-suspension system fitness. Although this case was very aggressive compared with everyday scenario, the effectiveness of the SSMS was clearly illustrated.

This technology permits amputees to realize continuous monitoring of their socket, which usually cannot be done by patients with neuropathy or other debilitating conditions.eover, a sensor system according to principles of the present invention provides a lost cost design in which the sensor cost is low, the system can be mounted on almost any sockets directly; the system is convenience to use, which amputees could install the sensor themselves; and allows clinicians to use collected information to make predictive intervention. In addition, insurance companies could use this system to collect data to choose appropriate technologies to use.

A continuous socket/suspension monitoring system according to principles of the present invention thus tracks relative displacement between amputee residuum and their socket using magnetic sensors. And therefore can provide a prosthesis suspension system that can alter the distribution of pressure within the prosthetic socket. As such, the resulting system can provide a low cost design, including a low cost sensor system which is socket independent. Amputees can install the sensor themselves because it is easy to install and convenient. Continuous monitoring can provide information to improve care for patients.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A monitoring system for amputees having a prosthesis having a socket, comprising:
   a residuum liner;
   at least one magnet affixed to the residuum liner; and
   a plurality of magnetic sensors in the socket,
   wherein the at least one magnet is movable toward and away from at least one of the magnetic sensors, such that a central axis of the at least one magnet moves closer to and further away from a central axis of at least one of the magnetic sensors, wherein the movement of the magnet toward and away from at least one of the magnetic sensors is lateral movement.

2. The monitoring system of claim 1, further comprising a measurement block housing the plurality of magnetic sensors.

3. The monitoring system of claim 2, the measurement block further comprising a plurality of amplifiers.

4. The monitoring system of claim 3, wherein the measurement block is attached to an external surface of the prosthesis.

5. The monitoring system of claim 1, wherein the plurality of magnetic sensors comprises multiple anisotropic magnetoresistive (ANIR) sensors.

6. The monitoring system of claim 1, further comprising a data acquisition board in communication with the plurality of magnetic sensors.

7. The monitoring system of claim 1, wherein the plurality of magnetic sensors are adjustably coupled to the socket.

8. The monitoring system of claim 1, wherein the magnetic field of the at least one magnet is positioned to provide an electronically measurable output angle with respect the at least one sensor, and wherein movement of the at least one magnet changes the output angle.

9. A method of monitoring motion of a residuum in a prosthesis, where the residuum is covered by a liner including at least one magnet and the prosthesis includes a plurality of magnetic sensors, the method comprising:
   identifying a location of the magnet in electromagnetically measurable proximity to at least one of the magnetic sensors; and
   identifying displacement of the magnet from the at least one magnetic sensor,
   wherein the magnet is movable toward and away from at least one of the magnetic sensors, such that a central axis of the at least one magnet moves closer to and further away from a central axis of at least one of the magnetic sensors, wherein the movement of the magnet toward and away from at least one of the magnetic sensors is lateral movement.

* * * * *